US007227957B2

(12) United States Patent
Cheng

(10) Patent No.: US 7,227,957 B2
(45) Date of Patent: Jun. 5, 2007

(54) NOISE-SUPPRESSING RECEIVER

(76) Inventor: Ziyi Cheng, 4 Bld 4 Dr. Apt 501, Fenghe Dong Yuan, Baidi Rd., Nalkai Distr, Tianjin (CN) 300190

( * ) Notice: Subject to any disclaimer, the term of this patent is extended or adjusted under 35 U.S.C. 154(b) by 844 days.

(21) Appl. No.: 10/297,901

(22) PCT Filed: Jun. 8, 2001

(86) PCT No.: PCT/CN01/00926

§ 371 (c)(1),
(2), (4) Date: Dec. 9, 2002

(87) PCT Pub. No.: WO01/97563

PCT Pub. Date: Dec. 20, 2001

(65) Prior Publication Data

US 2003/0138111 A1 Jul. 24, 2003

(30) Foreign Application Priority Data

Jun. 9, 2000 (CN) ................................ 00 1 18339
Nov. 3, 2000 (CN) ................................ 00 1 31990
Feb. 9, 2001 (CN) ................................ 01 1 02488

(51) Int. Cl.
*A61F 11/06* (2006.01)

(52) U.S. Cl. ...................................... 381/71.6; 181/206

(58) Field of Classification Search .............. 381/71.5, 381/71.6, 71.1, 74, 318, 322, 324, 312, 94.1; 781/206
See application file for complete search history.

(56) References Cited

U.S. PATENT DOCUMENTS 4,665,549 A * 5/1987 Eriksson et al. ........... 381/71.5
5,136,639 A * 8/1992 Brito .......................... 379/441
5,251,263 A * 10/1993 Andrea et al. ............. 381/71.6
6,415,034 B1 * 7/2002 Hietanen .................. 381/71.6

* cited by examiner

*Primary Examiner*—Ping Lee

(57) ABSTRACT

A noise-suppressing receiver is provided. A noise pick-up and a receiver are fixed within a cylinder-like body. An insulation layer is set between the noise pick-up and the receiver. The insulation layer divides the cylinder-like body into a receiver module and a noise-collecting module. A reticulate cover is provided at an end of the cylinder-like body, and a front cap is provided on the other end. A circuit device is added onto the inner side of the front cap described above. The invention has the stronger capability of attenuating environmental noise and the good effect of suppressing noise, because of its unique structure and the corresponding circuit device.

15 Claims, 31 Drawing Sheets

NOISE-SUPPRESSING RECEIVER

FIELD OF THE INVENTION

The invention relates to a receiver for attenuating the environmental noise, a receiver for attenuating the short distance noise, and a receiver for receiving and attenuating the environmental noise alternatively, especially to a design structure and a design method on an open-style noise-suppressing receiver.

BACKGROUND OF THE INVENTION

When living and working in a high noise environment, the environmental noise harms human health greatly, and at the same time, high noise may have influence on the capability to distinguish useful sound signals from noise. Therefore, an electrical device, which can attenuate noise and receive sound signals clearly, is required. At present, an existing source noise-suppressing receiver has some shortcomings.

The scheme disclosed in U.S. Pat. Nos. 5,889,875 and 5,917,923, two series acoustic chambers can suppress the influence of the distance from the noise source direction in the noises input from every sound inlet, thus making the noise picked up by the noise pickup in front of the one of the multiple sound inlets be in conformity with the noise input from every sound inlet, but followings are its shortcomings:

1. As such noise-suppressing receiver with two series acoustic chambers belongs to open or semi-open one and has larger volume, and it is farther from the sound inlet of the pickup to ear root, the noise-suppressing receiver has good noise-suppressing effect only for the noises produced from the same side noise source. With the noises of the opposite side, because of sound velocity, a larger time difference between the time from the sound source to the sound inlet of the sound chamber and the time from the sound source to the ear root is produced. As a result, it will be difficult to simultaneously suppress noises from both sides of the environmental noises leaked from the ear root to the inner ear because it is impossible to make suitable and corresponding phase shift to the noise with different distance and sound intensity, which will cause bad effect for suppressing noise from either side.

2. The environmental noise input from the external sound inlet goes to the vibration diaphragm of the backside of the speaker only through internal sound inlet, instead of to the auditory meatus in front of the vibration diaphragm of the speaker. On the same time, it has to the selectivity to the frequencies passed, so it is a semi-open sound inlet channel and cannot cancel the environmental noise leaked from the gap between the edge of noise-suppressing receiver and the skin.

3. In order to reduce the probability that the echoes sounded from the receiver are re-picked up by the environmental noise pickup, the receiver is placed farther from the microphone, and there is a sound insulation cushion ring around the touch part between the ear enclosure and the skin of the ear root. Therefore, its volume is larger and its noise suppressing effect is not perfect yet 4. Because of larger volume, it is suitable only for head-wearing use and cannot be used for small-size noise-suppressing receiver, such as earphone, in-ear-phone, auditory meatus style or deep auditory meatus style phone.

When people are near to a high noise sound source, because the sound signal with high noise sound intensity will cover over other useful sound signals, it becomes necessary to develop a pickup that can attenuate the sounds produced by the sound source near the receiver and can receive the sounds produced by the farther sound source, in order than the person under such environment can hear the sounds produced by the sound sources around.

OBJECT OF THE INVENTION

An object of the invention is to provide a noise-suppressing receiver. The receiver has an so-called open-style channel, through which the environmental noise can go into the ear to promote noise-suppressing performance.

Another object of the invention is to provide a noise-suppressing receiver, which can be made into small size products for easy in carrying about such as earphone, in-ear-phone, auditory meatus style or deep auditory meatus style phone.

Yet another object of the invention is to provide a noise-suppressing receiver, which uses a receiver module in the active noise-suppressing receiver to make a pickup which can attenuate the sound signals produced by the sound sources near the receiver module and can receive the sounds produced by farther sound sources. When a noise-receiving module is put at a place which is within tens of centimeters from the near field sound source, the noise-canceling pickup in the noise-collecting module will pickup the sound signals produced by the near field sound source to form a electric signals of the sound signals produced by the near field sound source.

Still another object of the invention is to provide a noise-suppressing receiver, which has an environmental noise pickup receive the electric signals of the mixed sound signals produced by near or farther field environment sound sources. Through a common-mode rejection circuit, the near field sound signal is removed from the sound electric signals picked up by those two kinds of pickups and the farther field sound signal is pickup up.

Another object of the invention is to provide a noise-suppressing microphone, characterized in that it has an environmental noise pickup and a noise-canceling pickup, the microphone includes a sound control switch device comprising an attenuating environmental noise status and a receiving environmental noise status, the switch device is controlled by the sound of speechmaker to switch over from the attenuating environmental noise status to the receiving environmental noise status or on the contrary; when the speechmaker is speaking, the microphone is switched to the status of attenuating environmental noise under the control of the sound control switch device; and when the speechmaker stops speaking, the microphone is switched to the status of receiving environmental noise under the control of the sound control switch device, so that the listeners can hear the environmental voice.

SUMMARY OF THE INVENTION

The invention is realized through the following method: a noise-suppressing receiver, a receiver (speaker) is set in a receiver module, characterized in that on the receiver module there is also a noise-collecting module and that in the noise-collecting module there placed an environmental noise pickup and a noise-canceling pickup.

Especially, the said receiver module and the noise-collecting module share a same shell. The main body of the shell is a cylinder, in which a partition layer is set to divide it into a receiver module and a noise-collecting module.

Especially, there is set an environmental noise pickup in the said noise-collecting module Especially, an end of noise pickup is fixed in the said cylinder and a front cover is covered on the end. There is set an inlet to the noise-collecting chamber on the sidewall of the noise-collecting chamber in the said cylinder.

Especially, in the said noise pickup module there are set multiple noise pickups and/or noise-canceling pickups. Between two adjoining noise pickups there is set a partition layer individually to divide the cylinder into several noise-collecting chambers. On the sidewall of each noise-collecting chamber there is set an inlet to the noise-collecting chamber.

Especially, a pair of noise pickup is placed in the same noise-collecting chamber.

Especially, it includes electrical circuit elements.

Especially, the said electrical circuit elements are any circuit or the combination of several circuits such as a print circuit board, a working circuit, an infrared receiving-transmitting device, a sound volume controller and a battery. On the print circuit board, there are placed the working circuit and/or the infrared receiving-transmitting device. The working circuit is communicated with the external circuit through leads. The infrared receiving-transmitting device is communicated with the external circuit through an antenna. The sound volume controller is connected with the working circuit and controls the sound volume of the open-style active noise-suppressing receiver. A battery supplies power to the working circuit, the infrared receiving-transmitting device.

Especially, the said working circuit includes the common-mode rejection circuit, and any circuit of the combination of several circuit such as an amplitude compensation circuit, a phase shift circuit, a time delay circuit and a frequency compensation circuit.

Especially, an end of the said receiver is fixed on the cylinder.

Especially, the said receiver includes a feedback pickup, which is in the front of the receiver.

Especially, on the sidewall of the cylinder, which is corresponding to the place of the receiver module, there are set several noise-entering slots of noise-entering tubes of the open-style sound wave entering channel.

Especially, the said receiver includes a acoustically transparent diaphragm that can let the voice in. The acoustically transparent diaphragm is located in the front of the receiver, so as to form a noise suppressing chamber between the front of vibration film of the speaker and the acoustically transparent diaphragm.

Especially, the said working circuit further includes a window comparator circuit with multi-intervals, which can adjust the amplification coefficient of the amplifier according to the receiving distance.

Especially, the said noise suppressing receiver includes amplifier circuits, which can adjust the amplification coefficient of the amplifiers according to the receiving distance.

Especially, a sound signal processing method, characterized in that a computing program is performed: converting the acoustical analogue electric signal picked up by the noise acoustical sensor into the digital signals with A/D converter; picking up from the sound signals picked up by one or more noise-canceling acoustical sensors the feedback sound wave signals picked up by the noise-canceling acoustical sensor and output from the speaker through the common-mode rejection operation by means of the running of the digital processor such as CPU, DSP, etc; performing the common mode rejection operation on the sound signals received by the environmental noise acoustical sensor and the feedback sound wave signals picked up by the noise-canceling acoustical sensor and output from the speaker to remove the feedback sound wave signal received by the environmental noise acoustical sensor and output from the speaker to eliminate the feedback noise due to the sound wave feedback caused by use of the “open-style sound wave entrance channel”, thus obtain the clearer environmental noise signal; performing the further operation such as phase shift and time delay; adjusting the size of the output signal from D/A converter with 180 phase difference with the environmental noise signal to offset against the environmental noise entered into the ears based on the size of the offset environmental noise signal picked up by feedback acoustical sensor; and outputting it from the D/A converter.

Especially, A sound signal processing method, characterized in that performing the common mode rejection operation on the feedback sound wave signals picked up by one or more noise-canceling acoustical sensors and output from the speaker, and the sound signals received by the environmental noise sensors with the feedback sound wave electric signals picked up by the noise-canceling acoustical sensor; to eliminate the feedback noise due to the sound wave feedback caused by use of the “open-style sound wave entrance channel”, thus obtain the clearer environmental noise signal; performing the further operation such as phase shift and time delay; adjusting the output signal from the speaker with 180 phase difference and equal in size with the environmental noise signal to offset against the environmental noise entered into the ears based on the size of the offset environmental noise signal picked up by feedback acoustical sensor.

Especially, the said noise-suppressing receiver can be various styles, such as an earphone, an in-ear-phone, an auditory meatus style or a deep auditory meatus style small-size active one.

Advantageous Effect

According to another aspect of the invention, a noise-suppressing microphone is provided, characterized in that there is a noise-collecting module over the microphone module, and there are set an environmental noise pickup and a noise-canceling pickups in the noise-collecting module.

According to another aspect of the invention, a noise-suppressing microphone is provided, characterized in that it has an environmental noise pickup and a noise-canceling pickup. The microphone includes a sound control switch device, which has attenuating environmental noise status and a receiving environmental noise status. The attenuating environmental noise status and the receiving environmental noise status may be switched over each other under the control of the sound of speechmaker.

When the speechmaker is speaking, the microphone is switched to the status of attenuating environmental noise under the control of the sound control switch device.

When the speechmaker stops speaking, the microphone is switched to the status of receiving environmental noise under the control of the sound control switch device, so that the listeners can hear environmental voices.

The noise pickups of the microphone (including environmental noise pickups, noise-canceling pickups and feedback pickups, etc.) can consist of various existing noise-canceling pickups and non-noise-canceling pickups as well as elements of every kind of pickup, which can be replaced each other for use.

The various types of acoustic sensors in the following table and other types are not listed in the table.

| | Classification | Sub- Classification | Materials |
|---|---|---|---|
| 1. Electromagnetic sound sensors | electro-dynamic sound sensors | moving-coil sound sensors, flat sound sensors, moving-coil sound sensors | Coil and magnet |
| | electromagnetic sound sensors magnetostrictive sound sensors | | Coil and magnet |
| 2. electrostatic sound sensors | electrostatic sound sensors | capacitor sound sensors, electret sound sensors, electrostatic sound sensors | Capacitor, power supply and electret |
| | piezo sound sensors | | piezoceramics, Rochelle salts, crystals, piezo polymers |
| | electrostrictive sound sensors | electrostrictive sound sensors, bimorph piezo sound sensors | Barium titanate ($BaTiO_2$), lead zirconate titanate (FZT) |
| 3. Resistor-transducing sound sensors | contact impedance sound sensors | granular carbon transmitters | Carbon and power supply |
| | impedance-transducing sound sensors | resistor-sensing sound sensors, semiconductor-sensing sound sensors | resistor-sensing gauge, semiconductor-sensing gauge, every kind of semiconductor sound sensors and power supply |
| 4. photoelectric sound sensors | phase-varying sound sensors | interference sound sensors, DAD sound sensors | Light source, Fiber-optical, light detector, Laser and detector etc. |
| | light-quantity-varying sound sensors | light-quantity-varying sound sensors | Light source, Fiber-optical, light detector, Laser and detector etc. |

Every kind of sound sensors and every kind of parts mentioned above can be exchanged each other for using. Of cause, the internal structure should be changed accordingly.

Similarly, the receiver can directly use existing every kink of speakers or speaker parts, which can be exchanged each other for using.

Those speakers include: electromagnetic conversion type speakers, electrostatic conversion type speakers, resistor conversion type speakers, photoelectric conversion type speakers and so on, in which 1. Electromagnetic conversion type speakers include electro-dynamic speakers, electromagnetic speakers and magnetostrictive speakers, etc. 2. Electrostatic conversion type speakers include electrostatic speakers, piezo speakers, electrostrictive speakers, etc. 3. Resistor conversion type speakers include contact impedance speakers, impedance conversion type speakers etc. 4. Photoelectric conversion type speakers include phase-varying speakers, etc, light-quantity-varying speakers. The electro-dynamic speakers include moving-coil speaker, flat microphone speakers and moving-coil speakers etc. The electromagnetic speakers include electromagnetic speakers etc. The magnetostrictive speakers include magnetostrictive speakers etc. The electrostatic conversion speakers include capacitor speakers, electret speakers and electrostatic speakers etc. The piezo speakers include those that made from piezoceramics, Rochelle salts, crystals and piezo polymers etc. The electrostrictive speakers include electrostrictive speakers and bimorph piezo speakers etc. The contact impedance speakers include granular carbon transmitters for use in telephone, etc. The impedance-conversion speakers include resistance-wire-sensing speakers, semiconductor-sensing speakers and semiconductor speakers etc. The photoelectric varying speakers include phase-varying speakers. The phase-varying speakers include interference speakers and DAD regeneration speakers. Besides, there are included light-quantity-varying speakers and other various speakers. Those speakers can also be divided into every detailed catalogues according the materials used. Every kind of speakers and every kind of parts mentioned above can be exchanged each other for using.

For the structure, the working principle and the working circuits of the noise-canceling pickup mentioned above, we can directly use the circuits disclosed in the noise-canceling pickups in the present inventor's CN Utility Model patent No. 98207092.6, CN Utility Model patent No. ZL99217256.X, CN Utility Model patent ZL 00 2 04563.X and CN Utility Model Applications PCT/CN99/00097, PCT/CN00/00357, and PCT/CN01/00108. It is able to add any of the combination of an amplitude compensation circuit, a phase shifter circuit, a time delay circuit and a frequency compensation circuit to common mode rejection circuits.

It is also able to set several open-style noise inlet slots or inlet pipes on the side-wall of the cylinder at receiver module that is corresponding to the place of the microphone module. When the open-style active noise-suppressing receiver is put in the ears of the user, an open-style environmental noise entrance channel is formed between the noise inlet slot and the skin in the ear, which can be called as "open-style sound wave entrance channel". Through the open-style sound wave entrance channel, external environmental noise is input to the ear channel part in front of vibration film of the speaker. As it let any frequency sound waves go through, so it is a full open sound entrance channel and the environmental noise is suppressed greatly.

Because "open-style sound wave entrance channel" is used, so the environmental noise pickup in the noise-collecting module can receive the feedback sound waves from the receiver to produce feedback noise.

A noise-canceling pickup can be set. The feedback pickup can be placed in the noise-collecting module to receive the feedback sound signals outputted from the receiving receiver. It can be used jointly with the feedback pickup or be used alone. An external environmental noise signal received by environmental noise pickup is passed through a common mode rejection circuit, and remove the feedback sound wave signal, which is received by the environmental noise pick up and then outputted from the receiver, so as to cancel the feedback noise from feedback sound waves caused by the open-style sound wave entrance channel.

A feedback pickup can be set. The feedback pickup can be located at the internal side of the net cover, or the rear or front or sidewall of the receiver. In addition, the feedback pickup can be wrapped in a pugging packing material. Under that condition, we can receive the feedback after-treated sound signal with that feedback pickup and the receiver. On basis of the feedback control principle, that feedback pickup can be used jointly with a noise-canceling pickup or used alone to further suppress the environmental noise in the external auditory canal. The feedback pickup can also be used for an acting noise-canceling microphone to pick up the rest after noise-suppressing sound waves and output the corresponding electric signal. Every pickup in the environmental noise receiver module can be made as individual one and separated each other, or all or some pickups are in a group.

An electric signal can be input by means of various signal transmitting methods such as a wire or wireless or infrared method. After processing by circuits, the input electric signal will be superposed onto the phase-shifted environmental noise electric signal and then output from the receiver. In the case that an active noise-suppressing receiver or a high noise-canceling pickup is used for the receiver, its noise-suppressing capability can be further increased so that the user can not only avoid the influence of the environmental noise, but also hear the input signal clearly. Because the sound signal processing circuit is very simple, so the cost will be reduced greatly, which will be good to use in every kind of high noise environment.

In order to meet the needs that the environmental noise signals received by the noise pickup have the same circumstance as that of the environmental noise signals entered into external auditory canal, there is set an open-style sound wave entrance channel between the part of the noise-collecting module and the part of the receiver module. In addition, there is set a sound inlet for the noise-collection chamber near the opening of the "open-style sound wave entrance channel". There is placed a noise-receiving pickup in the noise-collection chamber. Because the sound inlet for the noise-collection chamber is near the opening of the "open-style sound wave entrance channel", so the sound signal input from the inlet of the noise-collection chamber is about equal to the sound input from the opening of the "open-style sound wave entrance channel". Therefore, it is simpler to adjust the phase shift circuit and time delay circuit and is not necessary to adjust and correct them all the time.

The open-style active noise-suppressing receiver provided by the invention also includes a acoustically transparent diaphragm that can let the voice in. The acoustically transparent diaphragm is located in the front or the rear of the receiver, so as to form a noise suppressing chamber between the vibration film of the speaker and the acoustically transparent diaphragm. The acoustically transparent diaphragm can also be set at other places.

It is better that the said shell is an earphone, an in-ear-phone, an auditory meatus style or a deep auditory meatus style phone. Because of small size, it is easy to carry on and use. The difference among various small-size active noise-suppressing receivers such as an earphone, an in-ear-phone, an auditory meatus style and a deep auditory meatus style phone is the place where the receiver is put in the phone. Mostly, the receiver module is put outside of the external auditory canal for earphone style, not in the external auditory canal. For in-ear-phone style, the microphone module (noise-collecting module) is put in the external auditory canal mainly, and only the receiver module is in the external auditory canal. For auditory meatus style and deep auditory meatus style, both of the noise-collecting module and the receiver module are in the external auditory canal. Because of the limit caused by the placed position of the noise-collecting module in such small noise-suppressing receiver as the earphone, the in-ear-phone, the auditory meatus style and the deep auditory meatus style phones, the noise-canceling pickup in the noise-collecting module can not play its role and not pick up the feedback noise. As the noise-canceling pickup must be in an open space, a certain acoustic pressure between the front and rear sound inlets of the noise-canceling pickup can be produced for picking up the sound from the near field sound source. If a noise-canceling pickup is put in a close space, for example in the auditory meatus, as the auditory meatus is a tube-shape cavity, which is a relatively close space for the noise-canceling pickup in it, so a certain acoustic pressure between the front and rear sound inlets of the noise-canceling pickup can not be produced, and the noise-canceling pickup can not play its role in picking up the sound from the near field sound source. Therefore, in some circumstances the noise-canceling pickup can not be used in the noise-collecting module for the earphone, the in-ear-phone, the auditory meatus style or the deep auditory meatus style receiver and other small size receivers.

In order to prevent the insert earphone from falling down, a damping washer can be installed on its shell, which should be made of elastic materials with good acoustic permeability to environmental noise (for example, elastic rubber and sponge).

Generally, in order to ensure the same time deference and the same phase shift for the sound picked up by the noise pickup and the noise transmitted into the receiver in the ear, some measures are used. For example, a pickup shell with the same noise transmission route as that of noise on entrance into the ear on the pickup, or analog circuit and digital circuit, or orientation of pickup, or 0~360° of phase shift, or analog or digital time delay, or continuously adjusting phase shift circuit or amplifier circuit through digital circuit or comparison circuit by feedback pickup in the receiver. The technical measurements mentioned above can be used in reasonable arrangement to further improve noise-suppressing effects.

Through following schemes, the invention can eliminate the environmental noise and the self-excitation noise caused by the sound feedback in the case of using the "open-style sound wave entrance channel":

(1) Adding a cover or a sound collection cavity so as to make the sound waves received by the pickup be in conformity with entering-in-external-auditory-canal sound waves.

(2) Phase shift circuit: Analog phase shift circuit, digital phase shift circuit.

(3) Filter circuit: Sectional filtering, sectional phase shifting, Sectional filtering, Sectional time delay.

(4) Time delay circuit: Analog circuit, CCD circuit, digital circuit, DSP circuit.

(5) Internal pickup feedback circuit, controlling sound volume, Through digital spectrum analysis to find out self-excitation frequency, adjusting filter frequency band, filter out the sound waves in the frequency band, adjusting phase shift, time delay and sound volume.

(6) The acoustic characteristic of the sound collection cavity is same as that of external auditory canal, the sound wave transmission performance on its internal surface is same as that of the time interval from entering the inlet of external auditory canal after an earphone be wore to tympanic membrane.

(7) Using a sound feedback-canceling circuit or a sound feedback-canceling program to cancel the self-excitation caused by the sound feedback.

(8) Adding a acoustically transparent diaphragm that can let the voice in at the front end of the earphone to keep a fixed volume of sound neutralization cavity, which can reduce some parameter-uncertain problem (for example, impedance of the tympanic membrane). That measurement can well suppress environmental noise.

(9) The shape of the open-style active noise-suppressing receiver can follow after the shape of auditory meatus instead of the shape shown in the figure.

(10) To use the noise-canceling pickup to cancel the self-excitation noise produced by the sound wave negative feedback when an active noise-suppressing receiver is receiving the useful sound signal transmitted from the input sound signal in the case of using the "open-style sound wave entrance channel". If an active noise-suppressing receiver is not used for receiving the useful sound signal from the input sound signal, the noise-canceling pickups may not be used.

BRIEF DESCRIPTION OF THE DRAWINGS

The invention will be described in detail in conjunction with accompanying drawings in embodiments.

DETAILED DESCRIPTION OF THE INVENTION

What are described in the various embodiments can both be the relations on paper between attached drawings and the internal and external relations in actual applications between next to the internal acoustic meatus and external acoustic meatus.

Figure 1:
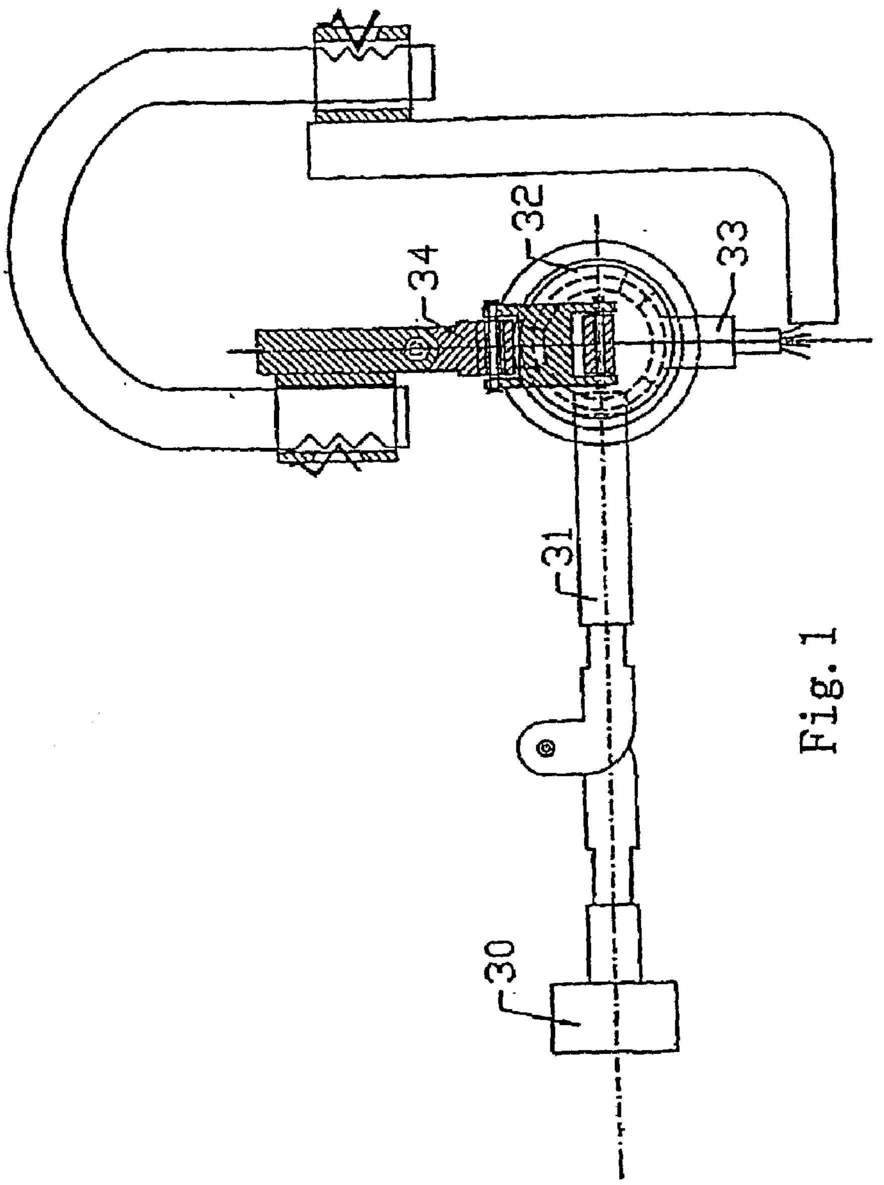
FIG. 1 is a sectional schematic view of an embodiment on the structure, in which an open-style active suppressing receiver provided by the invention is in combination with noise-canceling pickups.

Refer to FIG. 1. Acoustic noise-canceling pickup 30 is installed at the front end of the microphone support 31, whose rear end is connected with one end of the ear hanger 34. The same end of the ear hanger 34 is also connected with an open active acoustic noise suppressing receivers 32. 33 in the figure is lead-out wire. The noise-canceling pickup 30 in the figure is an acoustic noise-canceling pickup provided in the above-mentioned every patent and patent application technical scheme invented by me and ear hanger 34 uses an against-the-ear ear hanger.

Figure 2:
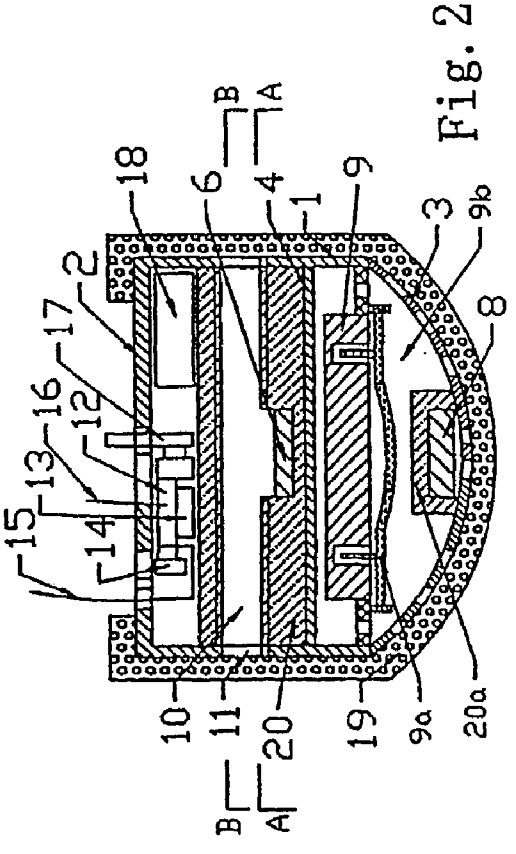
FIG. 2 is a sectional view of the first embodiment of an open-style active suppressing receiver.
Figure 2A:
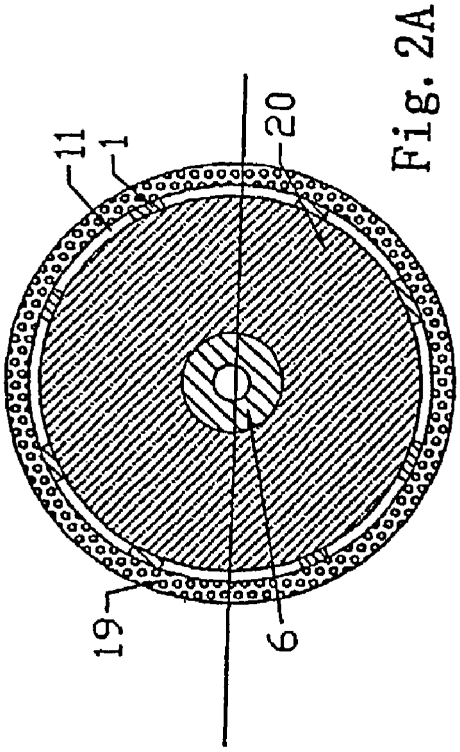
FIG. 2A and FIG. 2B are the sectional views along the lines of A—A and B—B shown in FIG. 2 respectively.
Figure 2B:
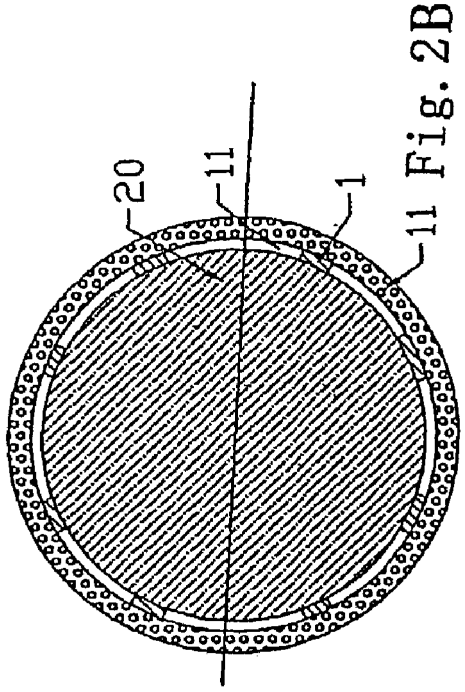

Refer to FIG. 2. Together with FIGS. 2A and 2B we can see that the front cover 2 and screen 3 are fixed on the both ends of cylinder 1, inside which are fixed the environmental noise pickup 6 and the speaker 9, which is located between the screen 3 and the environmental noise pickup 6. Partition layer 4 is available between environmental noise pickup 6 and speaker 9, which divided cylinder 1 into an acoustic noise suppressing receiver module and noise-collecting module. Environmental noise-collecting cavity entrance 11 can be found on the sidewall of cylinder 1 corresponding to environmental noise-collecting cavity 10. On the internal surface of front cover 2 is fixed printed circuit board 12, on which working circuit 13 and infrared receiving-transmitting device 14 can be found. Working circuit 13 communicates with external circuit through lead-out wires 16 and infrared receiving-transmitting device 14 communicates with external circuit through antenna 15. Volume adjuster 17 is connected with working circuit 13 to control the volume of this open active acoustic noise suppressing receiver. Working circuit 13 and infrared receiving-transmitting device 14 are provided with working power source by battery 18. On the internal surface of screen 3 is fixed feedback pickup 8, which is in front of speaker vibrating diaphragm 9*a* and is enclosed by pickup anti-vibration pad 20*a*. Sound-proof fixation and anti-vibration pad 20 is installed between partition lay 4 and environmental noise pickup 6. From FIG. 2 we can also see that damping spacer 19 (made of sponge) is available outside of cylinder 1, front cover 2 and screen 3.

Figure 3:
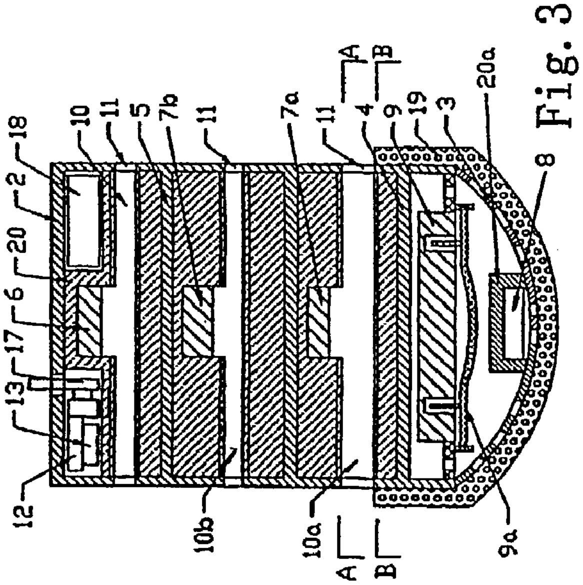
FIG. 3 is a sectional view of the second embodiment of an open-style active suppressing receiver.
Figure 3A:
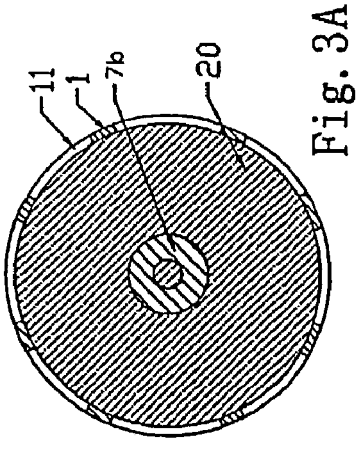
FIG. 3A and FIG. 3B are the sectional views along the lines of A—A and B—B shown in FIG. 3 respectively.
Figure 3B:
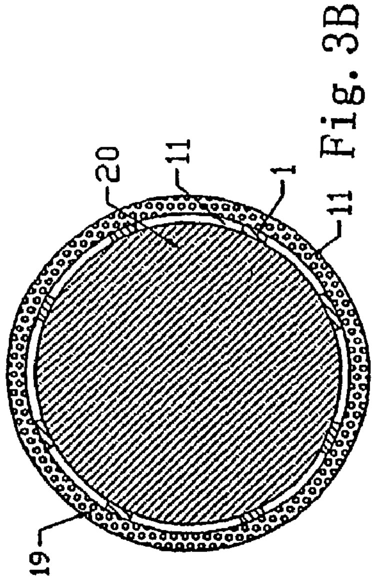

From FIGS. 3, 3A and 3B we can see that they differ from FIG. 2, in that: Since an open sound wave channel is available between environmental noise pickup 6 and speaker 9, acoustic noise-canceling pickups 7*a* and 7*b* are placed inside environmental noise collection cavities 10*a* and 10*b*. Environmental noise collection cavities 10, 10*a* and 10*b* are separated by pickup partition layer 5. Common mode rejection circuit 13 can remove the feedback sound wave electric signals of the sound wave signals outputted from speaker 9 and received by environmental noise pickup 6 to eliminate the feedback noises triggered by sound wave inverse feedback and caused by the use of "open sound wave entrance channel". Through Common mode rejection circuit 13, the sound wave electric signals picked up by noise-canceling pickups 7*a* and 7*b* can be removed of their environmental noise signals and a difference mode signal can be collected (feedback sounds output from speaker 9). This difference mode signal (feedback sound electric signal) can be provided with frequency compensation to compensate for the effects of acoustic noise-canceling pickup due to its different noise canceling effects at high and low frequencies. It can also be delayed for a certain time for synchronization with the sound electric signals picked up by environmental noise pickup 6 (Since noise-canceling pickups 7*a* and 7*b* are nearer to speaker 9, sound output from speaker 9 will first reach them and then environmental noise pickup 6. There is a specific time interval between the two.). Then common mode rejection will be performed through the delayed difference mode signal and the signals picked up by environmental noise pickup 6 to eliminate feedback sound electric signals and keep environmental noise electric signals. The environmental noise pickup 6 is installed in environmental noise-collecting cavity 10 and noise-canceling pickups 7*a* and 7*b* can eliminate environmental noise signals through Common mode rejection circuit 13. Common mode rejection can also be performed directly between the difference mode signal collected and the signals picked up by environmental noise pickup 6.

In various embodiments of the acoustic noise suppressing receiver in the invention, acoustic noise-canceling pickup can use the ones provided in the above patent and patent application schemes invented by me respectively based on the design requirement requirements. It can also use other acoustic noise-canceling pickups and non-acoustic noise-canceling pickups, or use environmental noise pickup 6 only. Noise-canceling pickups 7 and 7*a* can use a common non-acoustic noise-canceling pickup which is the same as environmental noise pickup 6. Acoustic noise-canceling pickups and environmental noise pickups can be placed in the same direction or opposite direction or face each other, etc.

Figure 4:
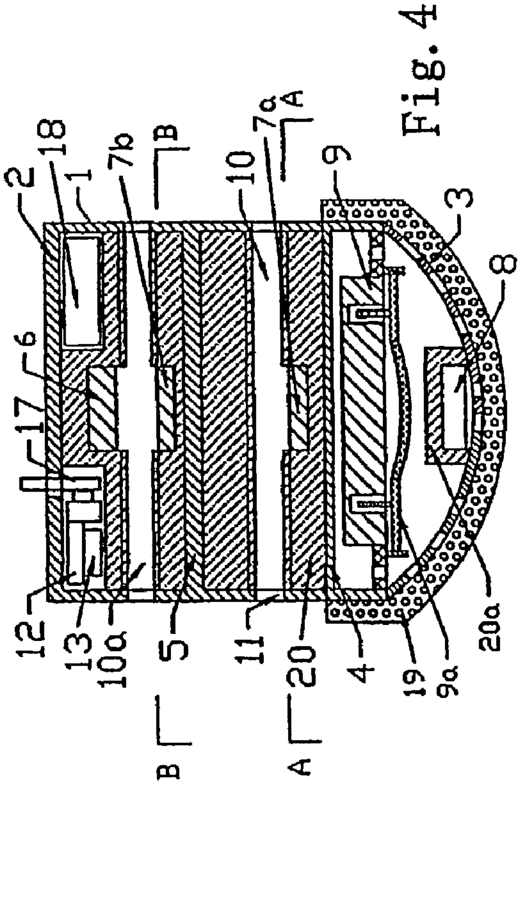
FIG. 4 is a sectional view of the third embodiment of an open-style active suppressing receiver.
Figure 4A:
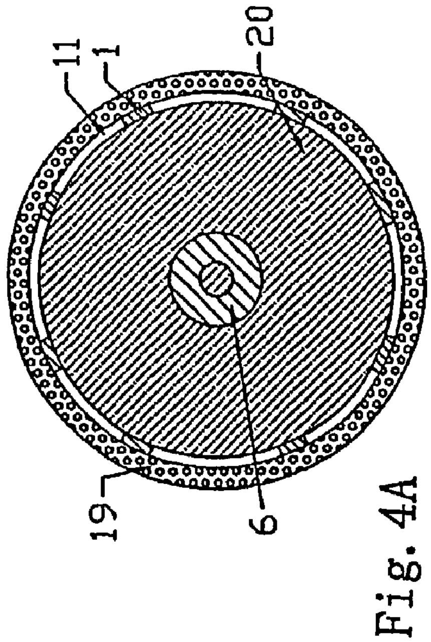
FIG. 4A and FIG. 4B are the sectional views along the lines of A—A and B—B shown in FIG. 4 respectively.
Figure 4B:
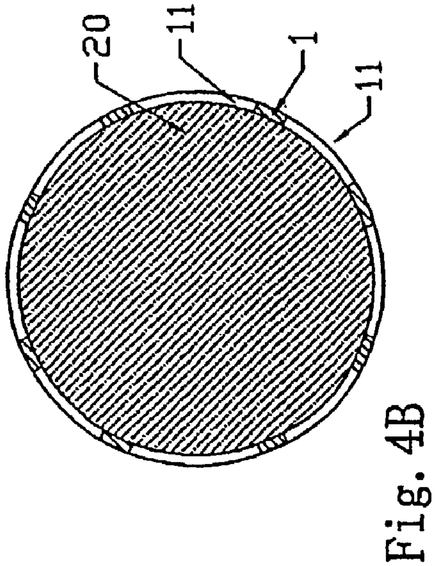

From FIGS. 4, 4A and 4B we can see that the difference between FIGS. 4 and 3 lies in: noise-canceling pickup 7*a* is placed inside environmental noise-collecting cavity 10 and noise-canceling pickups 7*b* and environmental noise pickup 6 are placed inside environmental noise-collecting cavity 10*a*, thus reducing an environmental noise-collecting cavity.

Figure 5:
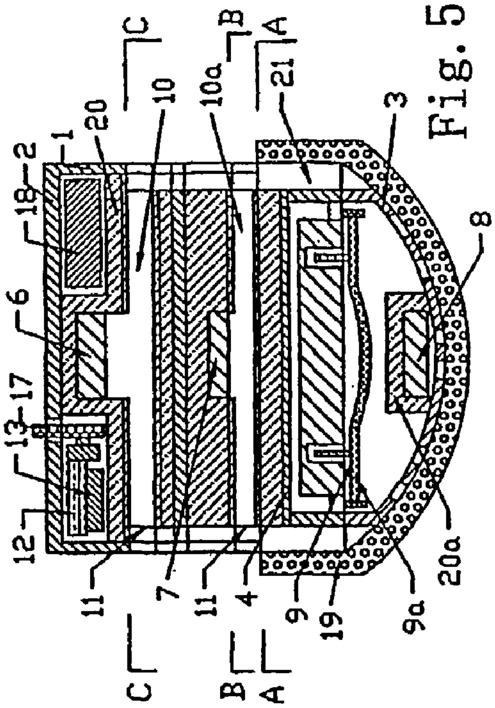
FIG. 5 is a sectional view of the fourth embodiment of an open-style active suppressing receiver.
Figure 5A:
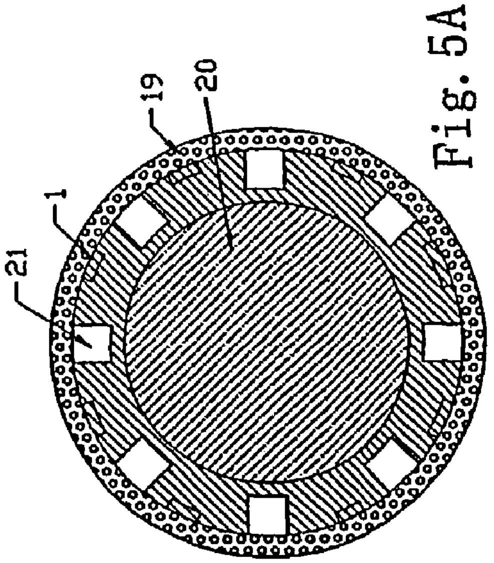
FIG. 5A, FIG. 5B, and FIG. 5C are the sectional views along the lines of A—A, B—B and C—C shown in FIG. 5 respectively.
Figure 5B:
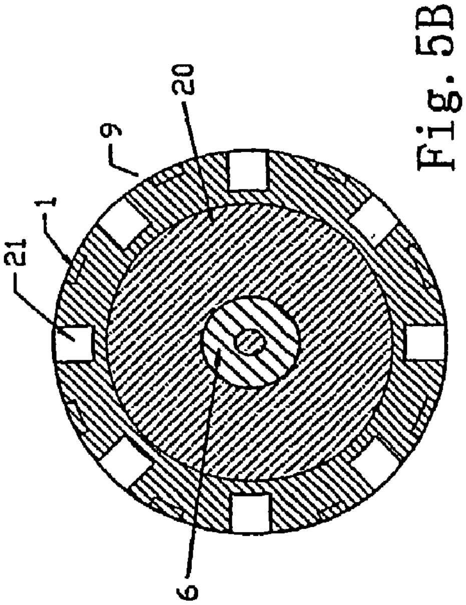
Figure 5C:
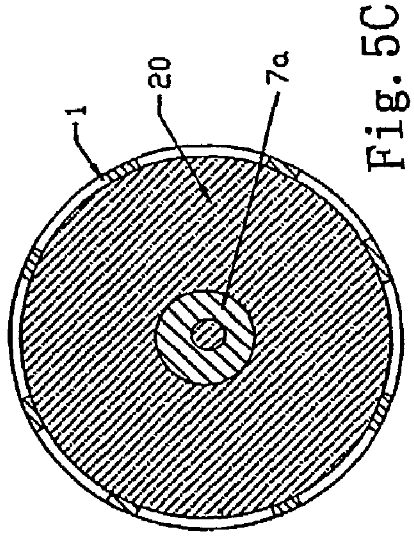

From FIGS. 5, 5A, 5B and 5C we can see that the difference between FIGS. 5 and 3 lies in: A noise-canceling pickup 7 is placed inside environmental noise-collecting cavity 10*a*, which is an acoustic noise-canceling pickup involved in several previous of the present inventor. The noise-canceling pickup 7 and environmental noise pickup 6 receive outside environmental noises and the electric signals of the sound wave signals output from speaker 9. The two remove the feedback sound wave electric signals of the sound wave signals output from speaker 9 and received by environmental noise pickup 6 through the common mode rejection circuit to eliminate the feedback noises triggered by sound wave negative feedback caused by the use of the "open sound wave entrance channel". Noise-canceling pickup 7 can use a common pickup which is the same as environmental noise pickup 6 to amplify the sound wave electric signals picked up by one of the environmental noise pickup 6 and noise-canceling pickup 7 into two paths of electric signals. One path of electric signals and the sound electric signals picked up by another pickup will obtain difference mode signal (feedback sound of the sound output from speaker 9, which is in fact an acoustic noise-canceling pickup) through common mode rejection circuit 13. Common mode rejection operation is performed between this difference mode signal (feedback signal of feedback sound) and the other path of sound electric signal to eliminate the feedback signal of feedback sound and keep environmental noise signal. The environmental noise-collecting cavity 10*a* and environmental noise-collecting cavity 10 are substantially of the same shape.

Noise entrance channel 21 can either be open or half-open. One or several can be used. It can either be a noise entrance slot or a noise entrance tube. We can also use the opening noise entrance channel formed by the clearance between the edge of cylinder 1 and the skin of the ear rather than noise entrance channel 21. The noise entrance channel 21 on cylinder 1 can effectively avoid the changes in environmental noise sound waves entering the ear when this open-style active acoustic noise suppressing receiver is placed in the ear too tightly and can eliminate environmental noises very satisfactorily.

Next to partition 4 is the environmental noise-collecting cavity entrance 11 of noise-collecting cavity 10, which can be opened on the extended section on environmental noise-collecting cavity entrance 11 of noise entrance channel 21, which sinks into cylinder 1. It can also be opened at other places.

Figures 6, 6A, 6B, 6C:
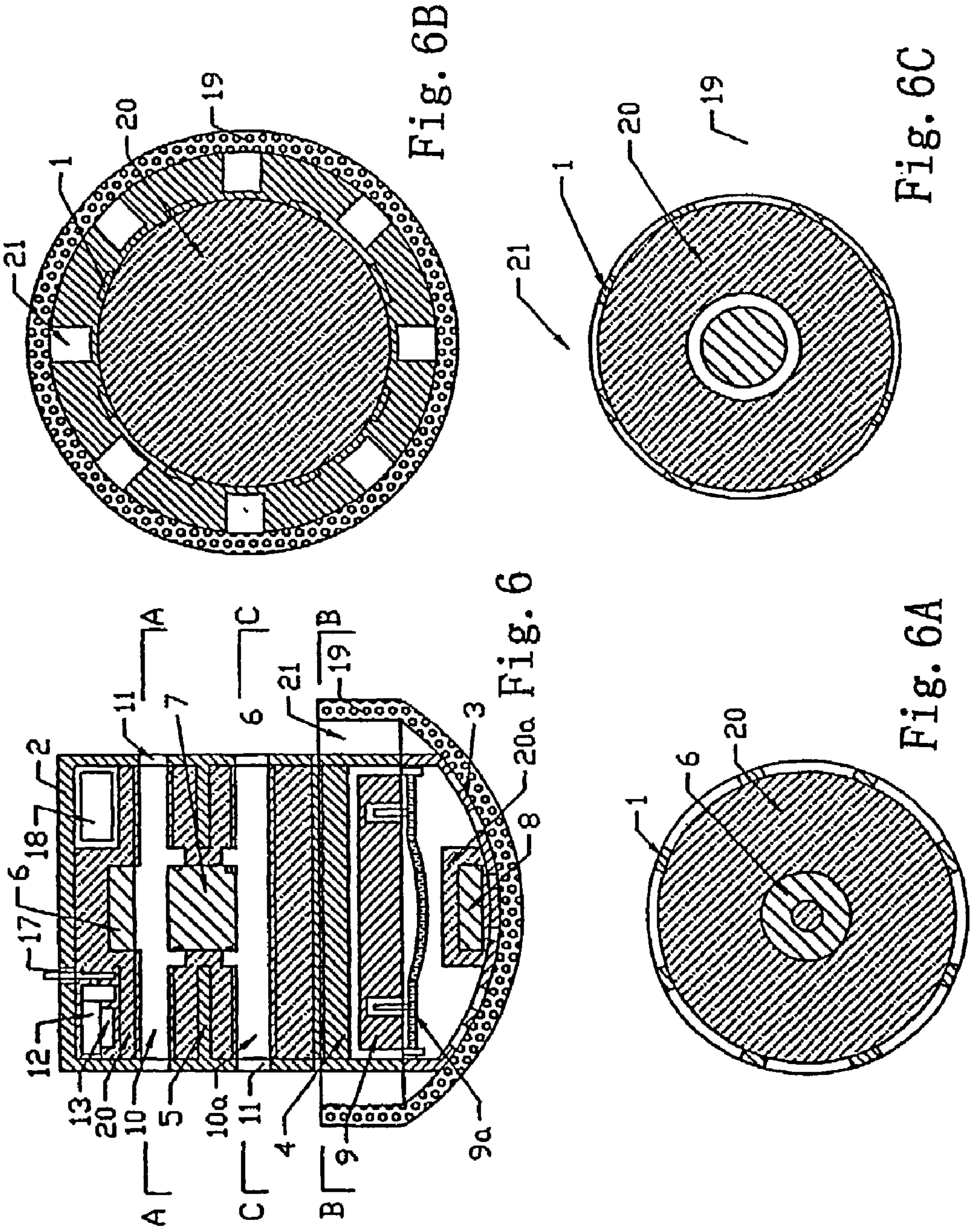
FIG. 6 is a sectional view of the fifth embodiment of an open-style active suppressing receiver.
FIG. 6A, FIG. 6B, and FIG. 6C are the sectional views along the lines of A—A, B—B, C—C shown in FIG. 6 respectively.
Figures 7, 7A, 7B, 7C:
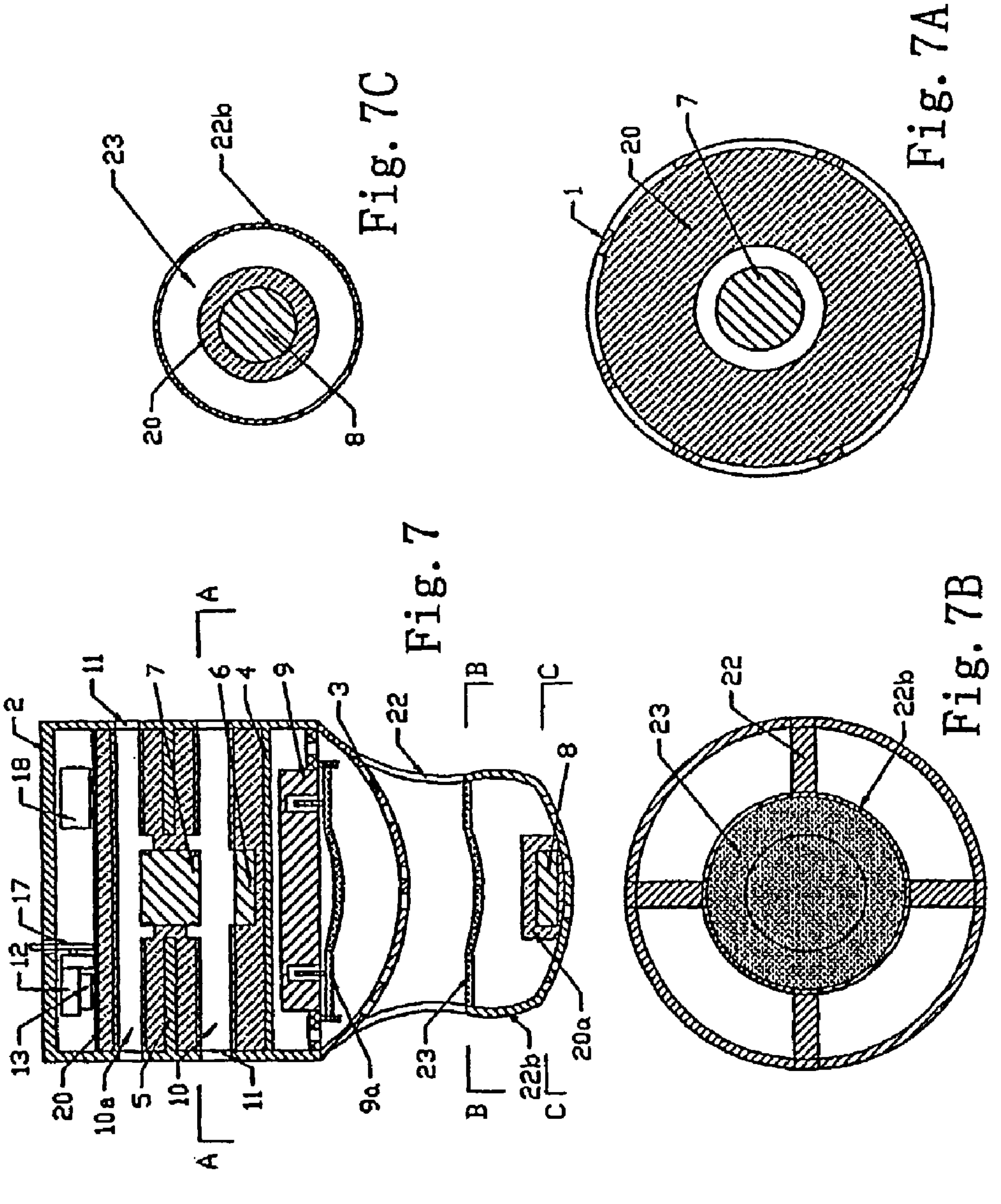
FIG. 7 is a sectional view of the sixth embodiment of an open-style active suppressing receiver.
FIG. 7A~FIG. 7C are the sectional views along the lines of A—A, B—B and C—C shown in FIG. 7 respectively.
Figure 8A:
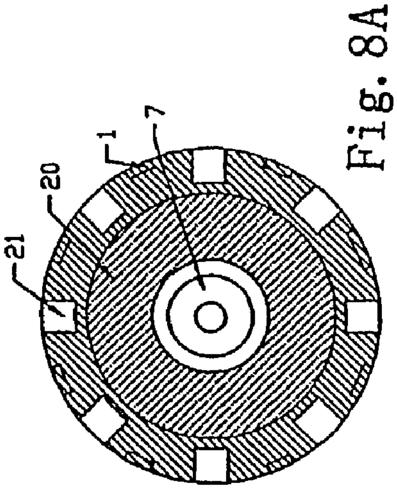
FIG. 8A~FIG. 8C are the sectional views along the lines of A—A, B—B and C—C shown in FIG. 8 respectively.
Figure 8B:
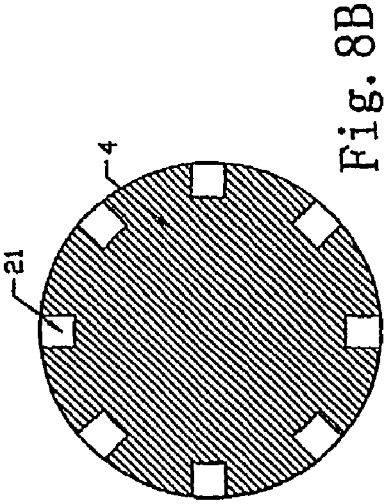
Figure 8:
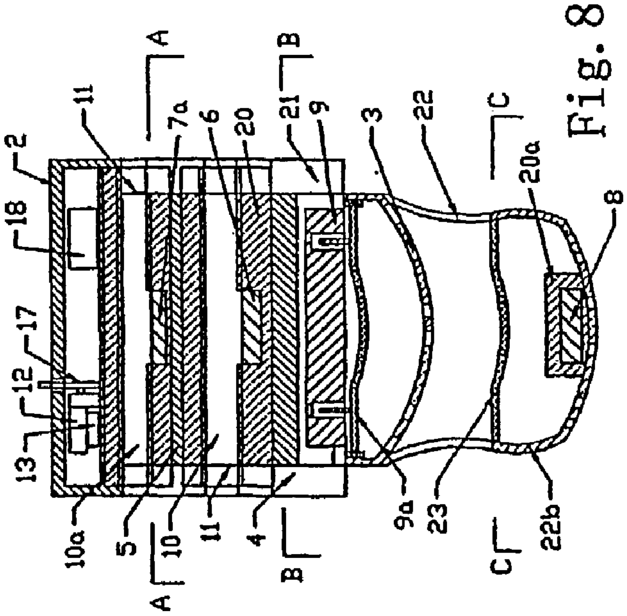
FIG. 8 is a sectional view of the seventh embodiment of an open-style active suppressing receiver.
Figure 8C:
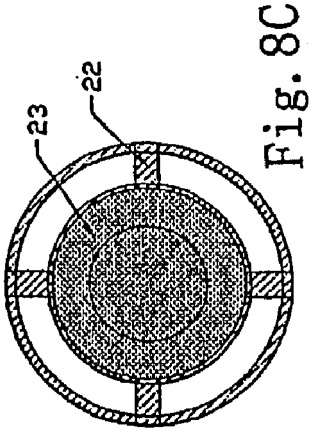

From FIGS. 6, 6A, 6B and 6C we can see that the difference between FIGS. 6 and 3 lies in: The noise-canceling pickup 7 which is placed inside noise collection cavities 10 and 10*a* is added in cylinder 1 of the noise-collecting module to eliminate the feedback noises due to the negative feedback of sound waves caused by the use of "open-style sound wave entrance channel". The noise-canceling pickup 7 directly picks up the feedback sounds output from speaker 9 and perform common mode rejection operation between this feedback sound electric signal and the sound signal picked up by environmental noise pickup 6 to eliminate feedback sound electric signal and keep environmental noise electric signal.

Likewise, noise entrance channel 21 is intended for solving the difficulty of environmental noise sound waves which can hardly enter the ear when this open-style active acoustic noise suppressing receiver is placed in the ear too tightly.

Noise-canceling pickup 7 can use one of the individual acoustic noise-canceling pickups involved in the inventions of acoustic noise-canceling pickups invented by the present inventor or other acoustic noise-canceling pickups.

Refer to FIGS. 7, 7A, 7B and 7C. Diaphragm support 22 is added in front of screen 3, namely in front of the speaker 9. An acoustically transparent diaphragm 23 can be found at the front end of diaphragm support 22. In this way, a sound wave acoustic noise canceling cavity is formed in the front of speaker vibrating diaphragm 9*a*, acoustically transparent diaphragm 23, diaphragm support 22 and the skin of the external auditory meatus, hence a sound wave acoustic noise canceling cavity with a fixed size. This can reduce the impacts of auditory meatus sound impedance on removal of noises, eliminate environmental noises effectively and reduce the negative feedback of sound waves. In the meantime, it allows useful sound signals coming in to pass through so that they can reach tympanic membrane to be heard by user. In addition, support 22*b* is also available in front of diaphragm support 22 and feedback pickup 8 and pickup anti-vibration pad 20*a* are moved to the internal surface of support 22*b*. It can be seen that a feedback pickup 8, which is fixed by sound-proof fixation anti-vibration pad 20 on the support is placed at the back of acoustically transparent diaphragm to receive sound signals which have been offset to adjust the phase of noise signals and the volume output from receiver to offset all outside noises that enter the external auditory meatus.

Refer to FIGS. 8, 8A, 8B and 8C. We can see that an acoustically transparent diaphragm 23 at the front end of diaphragm support 22 in FIG. 7 and the feedback pickup 8 fixed by anti-vibration pad 20 at the back of acoustically transparent diaphragm 23 are added on the basis of FIG. 5. The noise-canceling pickup 7 and environmental noise pickup 6 are all placed with their back against speaker 9.

Refer to FIGS. 9, 9A, 9B and 9C. We can see that acoustically transparent diaphragm 23 at the front end of diaphragm support 22 in FIG. 7 and the feedback pickup 8 fixed by anti-vibration pad 20 at the back of acoustically transparent diaphragm 23 are added on the basis of FIG. 6. The noise-canceling pickup 7 and environmental noise pickup 6 can be placed in this manner: one faces speaker 9 and one with its back against speaker 9.

Refer to FIGS. 10, 10A, 10B and 10C. We can see that speaker 9 is moved to diaphragm support 22*a* on the basis of FIGS. 5 and 7. The diaphragm support 22*a* can be constituted by the support with or without holes.

Refer to FIGS. 11, 11A, 11B and 11C. We can see that speaker 9 is moved to diaphragm support 22*a* on the basis of FIGS. 8 and 10.

Refer to FIGS. 12, 12A, 12B and 12C. We can see that speaker 9 is moved to diaphragm support 22*a* on the basis of FIGS. 8 and 10 and its cylinder 1 is slightly different from FIG. 11.

Figure 13A:
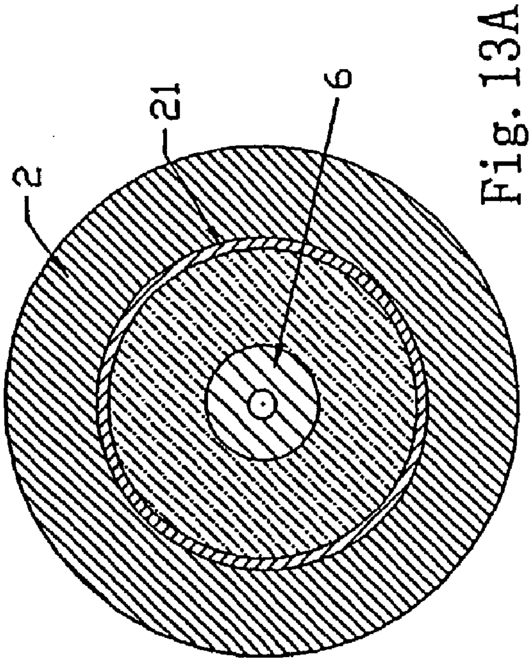
FIG. 13A and FIG. 13B are the sectional views along the lines of A—A and B—B shown in FIG. 13 respectively.
Figure 13:
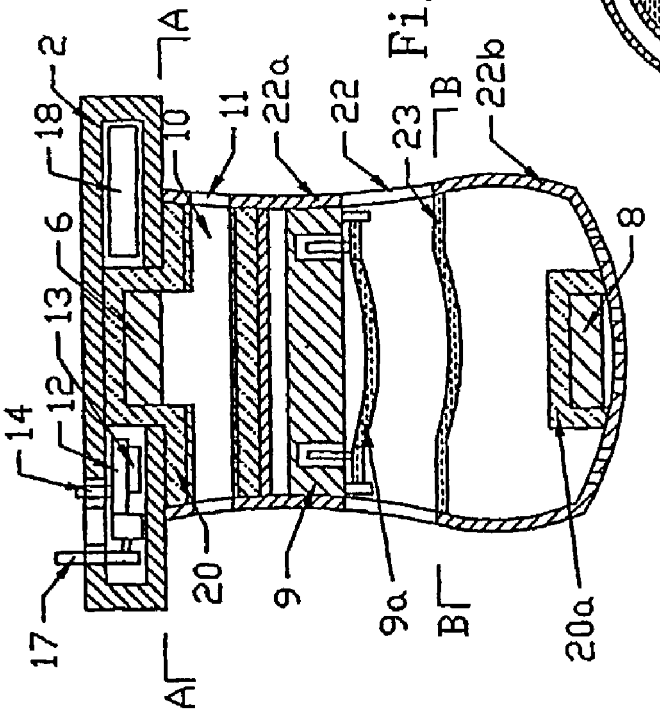
FIG. 13 is a sectional view of the twelfth embodiment of an open-style active suppressing receiver.
Figure 13B:
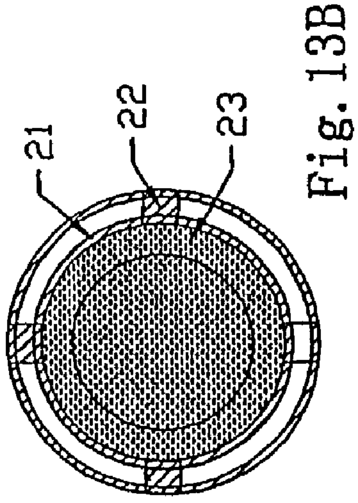

FIG. 13 (together with FIGS. 13A and 13B) has the following feature: environmental noise pickup 6, the speaker 9, environmental noise-collecting cavity 10 and environmental noise-collecting cavity entrance 11 are all moved to diaphragm support 22 in the same direction so that it can be used as an auditory meatus acoustic noise suppressing receiver.

Figure 14A:
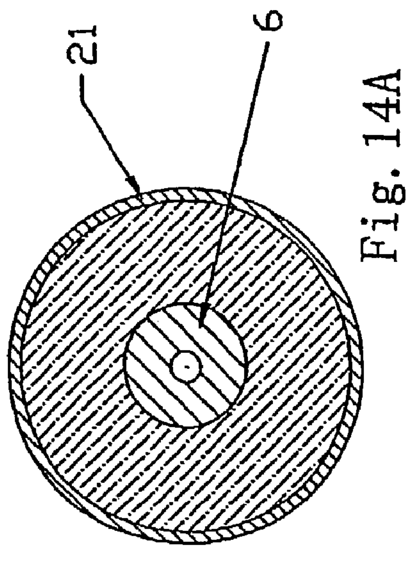
FIG. 14A and FIG. 14B are the sectional views along the lines of A—A and B—B shown in FIG. 14 respectively.
Figure 14B:
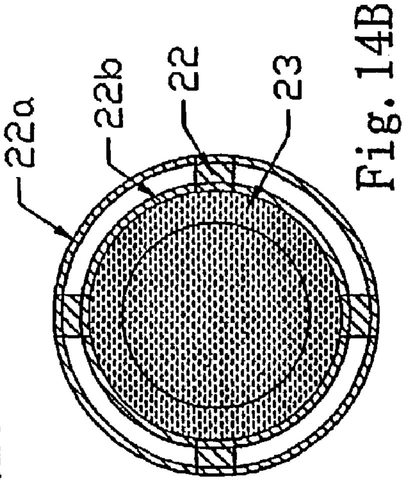
Figure 14:
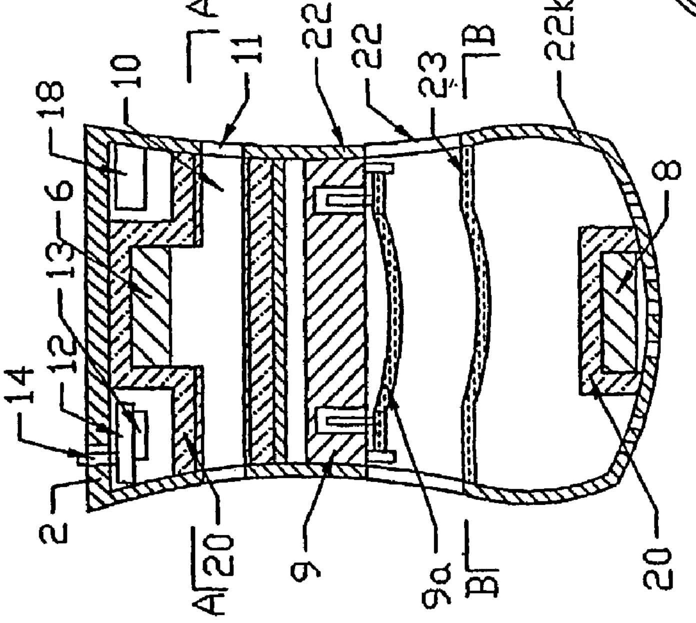
FIG. 14 is a sectional view of the thirteenth embodiment of an open-style active suppressing receiver.

FIG. 14 (together with FIGS. 14A and 14B) has the following feature: The outside diameter of cylinder 1 and front cover 2 are reduced so that it can be used as a deep auditory meatus acoustic noise suppressing receiver.

Figure 15A:
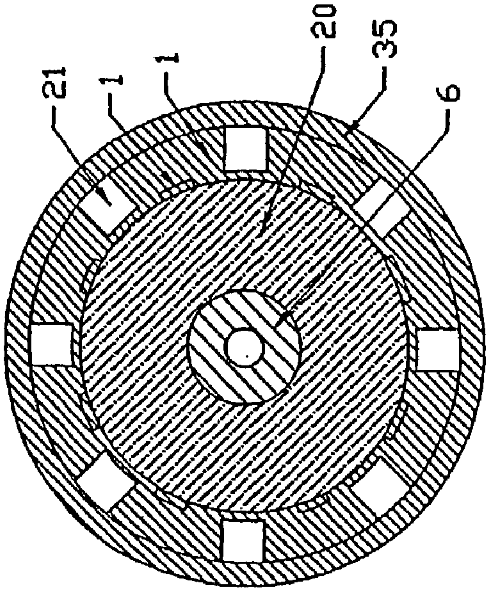
FIG. 15A is the sectional view along the line of A—A shown in FIG. 15.
Figure 15:
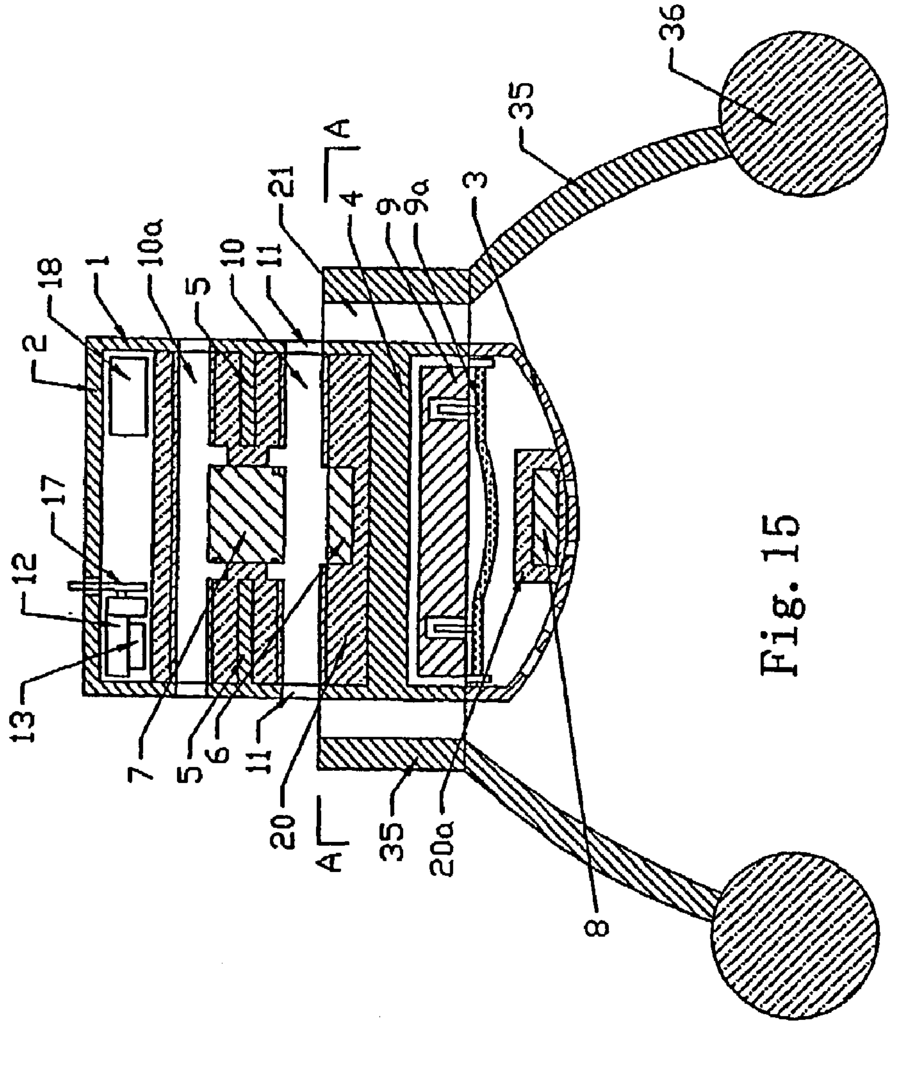
FIG. 15 is a sectional view of the fourteenth embodiment of an open-style active suppressing receiver.

FIG. 15 (together with FIGS. 15A and 15B) has the following feature: Noise entrance slot which is open at one side and totally opening is changed into a tube-shaped noise entrance channel 21 and ear pad support 35 and ear pad 36 are added. One end of ear pad support 35 is connected with cylinder 1 and the other end is connected with ear pad 36 so that it can be used as an against-the-ear noise suppressing receiver or ear muff noise suppressing receiver.

From the explanations to FIGS. 2 to 15 we can see clearly that generally speaking, this open-style active noise suppressing receiver consists of noise-collecting modules which are separated by partition layer 4 and form a whole and receiver module.

The receiver module consists of receiver module 9*b* under cylinder 1, which is separated by partition layer 4, speaker 9, which is placed inside receiver module 9*b*, screen 3 and sound-proof fixation anti-vibration pad 20*a* outside feedback pickup 8. When this open-style active noise suppressing receiver is placed in the ear, an opening environmental noise entrance channel is formed between the noise entrance channel 21 behind cylinder 1 and the skin inside the ear.

Noise-collecting module consists of environmental noise-collecting cavity 10 of cylinder 1 which is next to partition layer 4, environmental noise-collecting cavity entrance 11 and environmental noise pickup 6, which is placed inside environmental noise-collecting cavity 10. The environmental noise-collecting cavity entrance 11 is substantially opened near the open-style noise entrance channel 21. The acoustic features of the environmental noises picked up by environmental noise pickup 6 are basically similar to the environmental noise signals that enter the ear. Based on that whether environmental noise pickup 6 is be placed by facing speaker 9 or with its back against speaker 9, the phases of the noise signals received by it and the noise signals that enter the ear can either be the same, opposite or different at a certain angle. Based on the design requirement, their phases can be shifted by 0 to 360° by the phase shift circuit in working circuit 13 on printed circuit board 12. Phase shift and time delay can also be performed through the phase shift circuit and the time delay circuit so that when treated environmental noise signals which are output from speaker 9 and environmental noise signals that enter the ear through the open environmental noise entrance channel reach the same place inside the ear, their phase difference is at around 180° to eliminate outside environmental noises.

Various useful electric signals inputted by infrared receiving-transmitting device 14, antenna 15 and lead-out wire 16 are superimposed in the treated environmental noise signals output from speaker 9 through circuit 13 so that what are heard are useful sound signals whose environmental noises have been eliminated.

The sound-proof fixation anti-vibration pad 20 inside environmental noise-collecting cavity 10 can reduce the impacts due to the vibration of casing.

FIGS. 16 to 19 show the block diagram of the electric circuit of the open-style active noise suppressing receiver in the invention.

Figure 16:
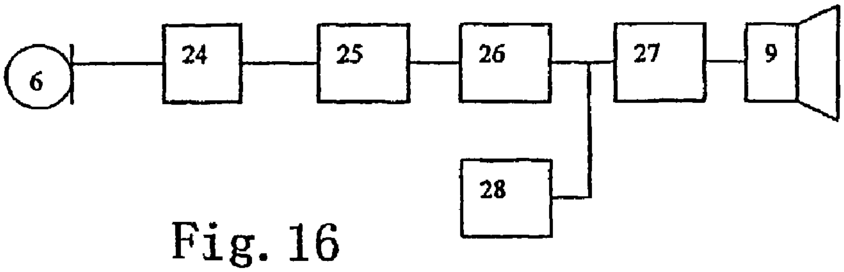
FIG. 16~FIG. 19 are block diagrams of illustrating the circuit parts of an open-style active noise-suppressing receiver according to the invention, respectively.

Refer to FIG. 16. The environmental noise pickup 6 receives outside environmental noises. Amplitude compensator 24 carries out amplitude compensation and phase shifter 25 performs 0 to 360° phase shift. After the amplitude of environmental noise pickup 6 is compensated by Amplitude compensator 24 and output circuit 27 performs signal power compensation, we can obtain sound wave signals with a phase difference of approximately 180° between the vibration output to speaker 9 through speaker vibration diaphragm 9*a* and the environmental noise sound wave signals that enter from outside and reach speaker vibration diaphragm 9*a*. Its principle is: If the phases of the two waves are opposite, the loose part of one wave will encounter the dense part of another wave. During transmission in the space, the two will weaken each other or be completely offset and their resultant amplitude is the difference between the two. Based on the design requirement, phase shifter 25 can use phase inverter circuit or added with time delay circuit 26. Electric signals input from outside are treated by electric signal input circuit 28 and are superimposed on environmental noise sound electric signals whose phase has been shifted and output circuit 27 performs power compensation and send them out to speaker 9 for output. When the environmental noise electric signals output from environmental noise pickup 6 do not at 0° or 180° with the environmental noise No. 1 pickup that enter from outside and reach speaker vibration diaphragm 9*a*, (when time delay is fixed), phase adjust circuit can be adjusted to adjust the phase difference of input voice signals so that their phase difference is around 0 or 180°. Or when phase difference is 0°, common mode rejection circuit can use subtraction circuit (differential amplification circuit). When phase difference is 180°, common mode rejection circuit can use adder circuit.

Based on the design requirement, we can decide whether to use phase shift circuit, time delay circuit, degree of phase shift, time of delay and whether all two circuits will be used or just one will be used.

Various types of analog signal phase shift circuits, time delay circuits, or various suitable digital signal phase shift circuits and time delay circuits can include various appropriate analog phase circuits, time delay circuits formed by active filter or passive filter or the combination of the two, or various appropriate bucket-brigade delay BBD or charge coupled device CCD and separate digital signal time delay circuits. The common mode signal rejection circuit can use: 1. making the two paths of signals offset to offset to each other with a balance bridge circuit which is often used in a phone circuit; 2. making the phase difference between two paths of signals be 180°, the making their phases offset to each other with an adder circuit; 3. making two paths of signals with the same phase subtract mutually with a subtraction circuit, such as differential amplifier circuit, etc.

Various circuits in FIGS. 16 to 19 can consist of analog circuits, or digital ones, or the combination of the two.

Digital phase shift, time delay and digital common mode signal rejection circuit can consist of a central processing unit CPU and a peripheral circuit or consist of a digital signal processor (DSP) and a peripheral circuit and run the corresponding programs. Likewise, the digital signal processing circuit can also consist of a central processing unit CPU and a peripheral circuit or consist of a digital signal processor (DSP) and a peripheral circuit. It can also consist of other digital circuits which can carry out this phase shift, digital delay and digital common mode rejection.

Figure 17:
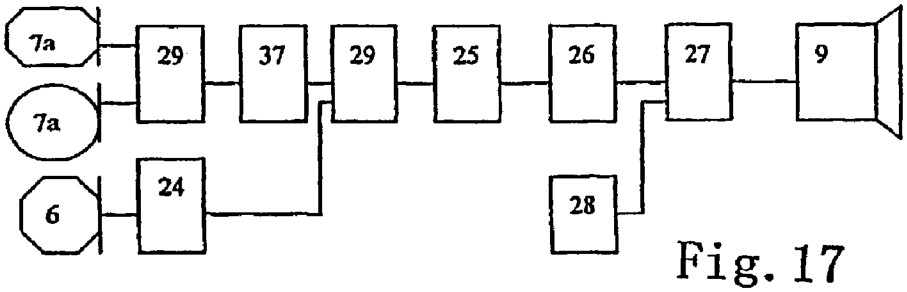

Refer to FIGS. 17 and 16. Their difference lies in: When we use the theories and circuits of various acoustic noise-canceling pickups provided in the above patent and patent application technical schemes invented by the inventor, two acoustic noise-canceling pickups 7 and 7*a* can be used to form one acoustic noise-canceling pickup through the common mode rejection circuit to pick up the received electric signals of the sound wave signals output from speaker 9. The time delay circuit can be used to delay the sound electric signals picked up by the acoustic noise-canceling pickup next to the receiver by a certain time. Then, for the delayed sound electric signals, the common mode rejection can be performed together with the sound electric signals picked up by another acoustic noise-canceling pickup to reduce the problem that the low frequency characteristic and the high frequency characteristic of the common acoustic noise-canceling pickups are not conform to each other. We can also perform frequency compensation first based on the design requirement and then perform common mode rejection with outside environmental noise electric signals received by environmental noise pickup 6. Electric signals whose amplitude is compensated by amplitude compensator 24. One or two of the two electric signals can be compensated by time delay circuit 37 to compensate for the time difference due to the difference in position. We can also not use time delay circuit and allow the two electric signals to pass through common rejection circuit to remove the feedback sound wave electric signals of the sound wave signals output from speaker 9 and received by environmental noise pickup 6 to eliminate the feedback self-excitation caused by the sound wave feedback output from speaker 9.

Figure 18:
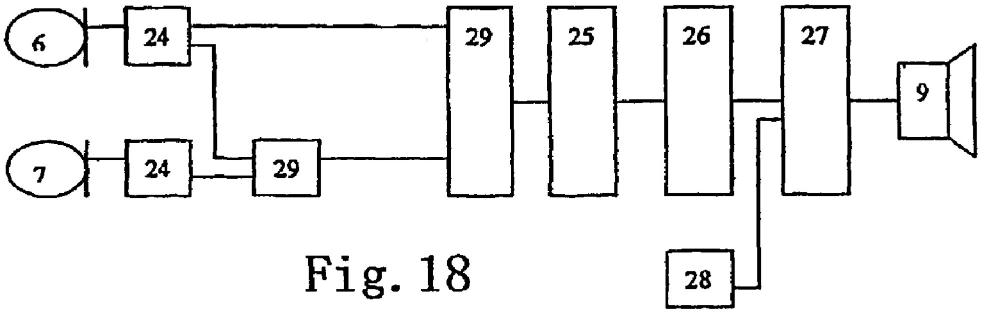

Refer to FIGS. 18 and 17. Their difference lies in: When the environmental noise pickup 6 is used as a common pickup of the environmental noise pickup and the acoustic noise-canceling pickup, the electric signals of the sound signals received by environmental noise pickup 6 whose amplitudes have been compensated by amplitude compensator 24 are divided into two paths. One path of the signals will form an acoustic noise-canceling pickup together with the sound signals picked up by noise-canceling pickup 7 and electric signals whose amplitudes have been compensated by amplitude compensator 24 through the common mode rejection circuit to collect the feedback sound wave electric signals of the sound wave signals output from speaker 9. The other path of the signals and the feedback sound wave electric signals output from the common mode rejection circuit pass through the common mode rejection circuit, to remove the feedback sound electric signals of the sound signals received by environmental noise pickup 6 and then output from speaker 9, and to eliminate the feedback noises due to the negative feedback of sound waves caused by the use of the "open-style sound wave entrance channel".

Figure 19:
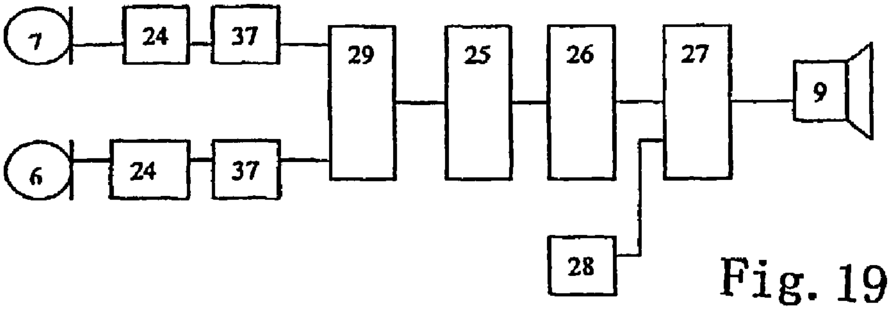

FIG. 19 shows the block diagram of the circuit in the acoustic noise suppressing receiver in the invention.

Refer to FIGS. 19 and 18. We can see that the difference lies in: When we use the sound wave signals of the sound wave signals output from pickup speaker 9 of the individual acoustic noise-canceling pickup 7 provided in the above patent and patent application technical schemes invented by me, they will be compensated by amplitude compensator 24. The environmental noise pickup 6 receives the sound wave electric signals output from outside environmental noises, which are also compensated by amplitude compensator 24. One or two of the two electric signals for which amplitude compensation were performed can be compensated by time delay circuit 37 to solve the time difference due to the difference in position. We can also not use the time delay circuit and allow the two electric signals to pass through the common rejection circuit to remove the feedback sound wave electric signals of the sound wave signals output from speaker 9 and received by environmental noise pickup 6 to eliminate the feedback noises due to the negative feedback of sound waves caused by the use of the "open-style sound wave entrance channel".

Figure 20A:
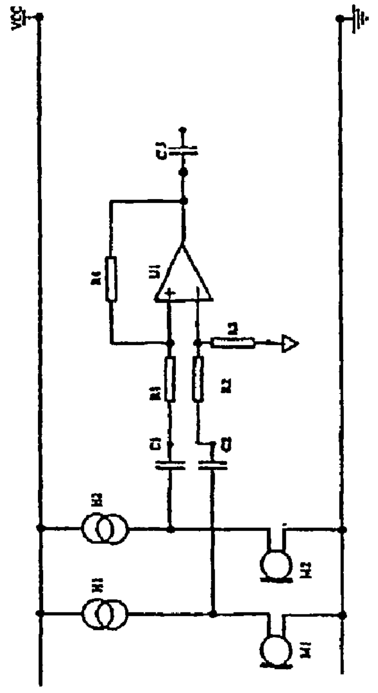
FIG. 20*a* is a basic circuit diagram of common mode rejection circuit that consists of subtracter circuits.

FIG. 20*a* is a common mode rejection circuit formed by a subtraction circuit. In the figure, one path is connected to a block capacitor C2 through an output terminal of the pickup M1 and is connected to the negative terminal of the common mode signal rejection circuit U1 formed by the subtractor through R2. The other path is connected with the positive terminal of the common mode signal rejection circuit U1 formed by the subtractor through C1 and C2 via an output terminal of the other pickup M2. Power source Vcc respectively supplies power to No. 1 and No. 2 pickups M1 and M2 through constant-current source H1 and H2 or the power supply circuit and resistors, common mode signal rejection is performed for the sound signals received by the two pickups through the common mode signal rejection circuit to pickup differential mode signals.

In this embodiment, the differential amplifier circuit is the LM324 one path operational amplifier. Other models and types of the operational amplifiers can also be used. And the said subtraction circuit can also use other types of the differential amplifier, such as in-phase series differential amplifier, in-phase parallel differential amplifier, etc. We can also use other types of the subtraction circuits consisting of transistors, operational amplifiers or digital circuits. This subtraction circuit can also be used in other pickup circuits that need the subtraction circuit to perform common mode signal rejection.

Figure 20B:
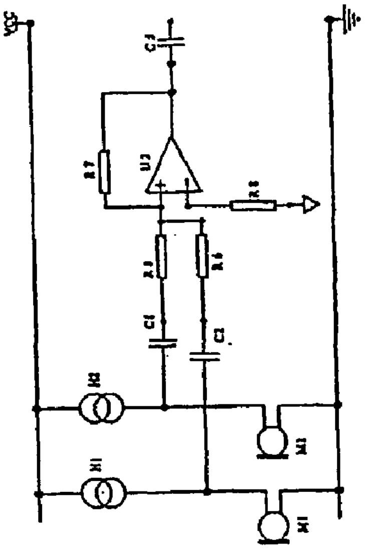
FIG. 20*b* is a basic circuit diagram of common mode rejection circuit that consists of adder circuits.

FIG. 20*b* is another common mode rejection circuit formed by an adder circuit. It shows that one path is connected to the block capacitor C2 through an output terminal of pickup M1. The other path is connected to the block capacitor C1 via the output terminal of pickup M2 to connect with the positive end of the common mode signal rejection circuit U2 formed by R5, R6 and R7 and the adder. The negative end of U2 connects with resistor 8. Power source Vcc supplies power to pickups M3 and M4 through the constant-current source H1 and H2 (or resistor and other power supply circuits). The output terminal will reject common mode signals to collect differential mode signals for further processing.

In this embodiment, the differential amplifier circuit is the LM324 one path operational amplifier. Other models and types of the operational amplifiers can also be used. And the adder circuit can also use the positive phase adder or the reverse phase adder consisting of transistor, operational amplifier or digital circuit. This adder circuit can also be used in other pickup circuits that need the adder circuit to perform the common mode signal rejection.

Figure 20C:
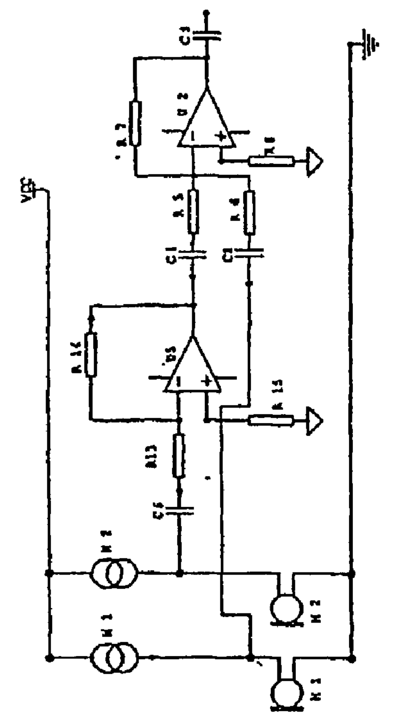
FIG. 20*c* is a basic circuit diagram of common mode rejection circuit that consists of phase shift circuit and adder circuits.

FIG. 20*c* is a common mode rejection circuit formed by a phase shift circuit and an adder circuit. It shows that it is a common mode rejection circuit formed by a phase shift circuit and an adder. Comparison between FIGS. 6*c* and $\mathbf{6}_B$ shows that a new phase shift circuit is added only in the case that the output terminal of pickup M2 is connected between the block capacitor C1 and the resistor R5 and the input of U2 is reversed, the same parts won't be explained and we just make a description of the phase shift circuit, which consists of the amplifier U5 and resistors R13, R14 and R15. One end of R13 and negative feedback resistor R14 is connected to the negative (−) end of U5 and the other end of feedback resistor R14 is connected with the output terminal of U5 and block capacitor C1. The other end of the capacitor C1 outputs signals. The positive (+) input of the amplifier U4 is grounded through R15.

This circuit is applicable to the case that when the sound signals received by the receiving end of two pickups do not have a phase difference of 0 or 180° exactly and the subtractor or the adder circuit thus cannot be used to perform the satisfactory common mode rejection, the phase difference can be corrected with this circuit, thereby perform the common mode rejection.

In this embodiment, the phase shift circuit can consist of transistor, operational amplifier or digital circuit. The above circuits have a phase shift of 180° and phase the shift circuit whose phase can be shifted within 360° can also be used subject to needs. In this embodiment, the phase shift circuit uses the LM324 two path operational amplifier or other models and types of operational amplifiers, or the phase shift circuit consisting of transistor, operational amplifier or digital circuit.

Figure 20D:
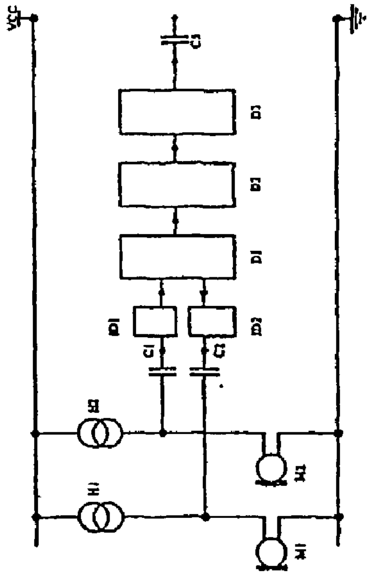
FIG. 20*d* is a basic circuit diagram of common mode rejection circuit and fixed-position receiving system that consist of A/D converter circuits.

FIG. 20*d* describes another type of common mode signal rejection circuit, namely, digital common mode rejection circuit and positioning receiving system circuit, which consists of analog/digital conversion circuit, CPU for common mode rejection operation and digital/analog conversion circuit and connects to capacitors C2 and C1*m* etc from pickups M1 and M2, etc. Their connection is the same as that of the FIG. 7*a*. Then, collected sound signals are input to such circuits as preprocessing circuit ID2 and ID1 and are then output to the analog/digital conversion circuit CD1 after various necessary preprocesses, to be converted from analog signals into digital ones. Analog/digital conversion circuit D1 can output converted digital signals to digital signal processing circuit CD2 for common mode signal rejection operation to remove common mode signals and collect differential ones. It can also perform positioning receiving operation and further digital processing, such as digital filtering, voice identification, etc. The digital signal processing circuit can also consist of other types of digital circuits. The differential mode signals collected by the digital common mode signal rejection circuit CD2 can be output to digital/analog conversion circuit CD3 and be converted into analog signals, which can be output to succeeding application circuits for further processing via block capacitor C5. The differential mode signals can also be used as the control signals of various sound signal control switches to control the various functions and circuits that must be controlled by sound signals. Digital signal processing circuit can also be used for further digital processing operation, such as digital filtering, sound identification, voice control, etc. They can also be output to input/output interface (I/O) circuit CD4 to control peripheral circuits, such as the switch circuit, etc. Comparison between the circuits in embodiments 7*a* and 7*b*, we can know that capacitors C6 and C7 are used for the frequency compensation of two pre-stage amplifier circuits respectively.

For instance, this digital common mode signal rejection circuit can either consist of CPU and peripheral circuits or digital signal processor (DSP) and peripheral circuit. Likewise, the digital signal processing circuit can also consist of other types of digital circuits which can perform this operation or other types of digital circuits with the same functions. All circuits in this circuit can use integrated circuit or discrete component circuits. Subject to needs, we can use analog circuit, digital circuit or the combination of the two, as well as various circuits that can carry out the functions of this circuit.

Figure 9A:
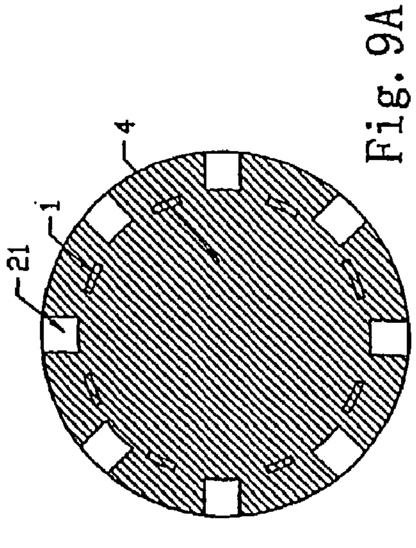
FIG. 9A~FIG. 9C are the sectional views along the lines of A—A, B—B and C—C shown in FIG. 9 respectively.
Figure 9B:
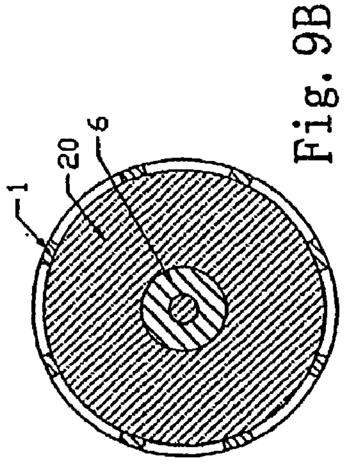
Figure 9:
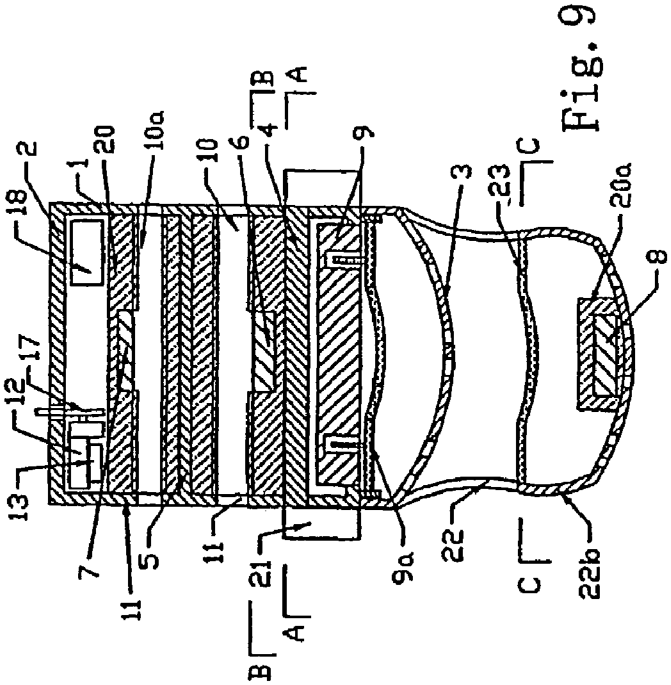
FIG. 9 is a sectional view of the eighth embodiment of an open-style active suppressing receiver.
Figure 9C:
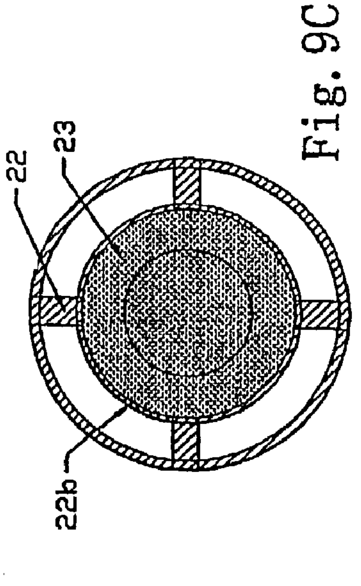
Figure 10A:
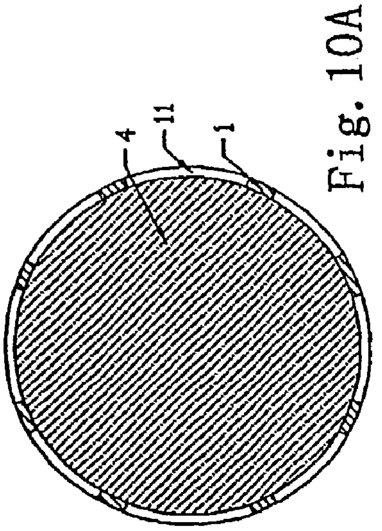
FIG. 10A~FIG. 10C are the sectional views along the lines of A—A, B—B and C—C shown in FIG. 10 respectively.
Figure 10B:
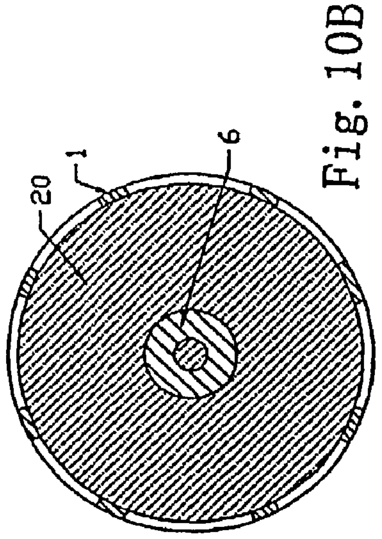
Figure 10:
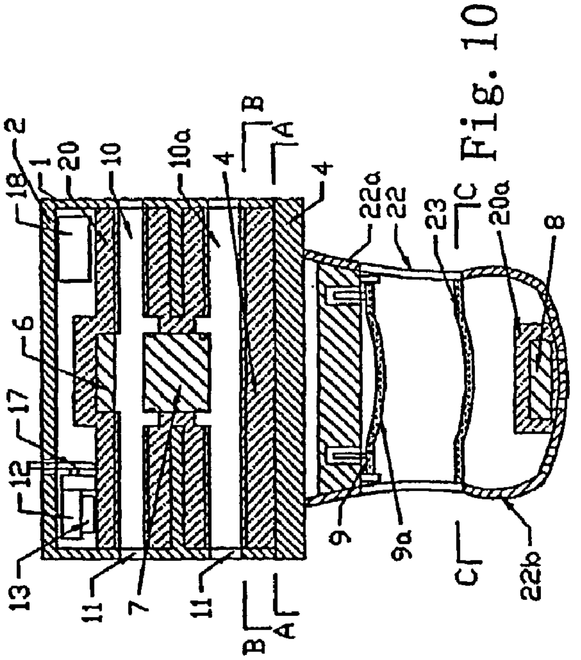
FIG. 10 is a sectional view of the ninth embodiment of an open-style active suppressing receiver.
Figure 10C:
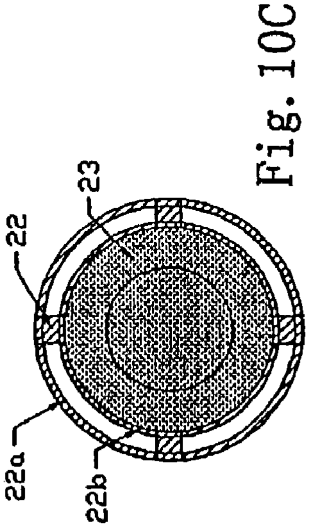
Figures 11, 11A, 11B, 11C:
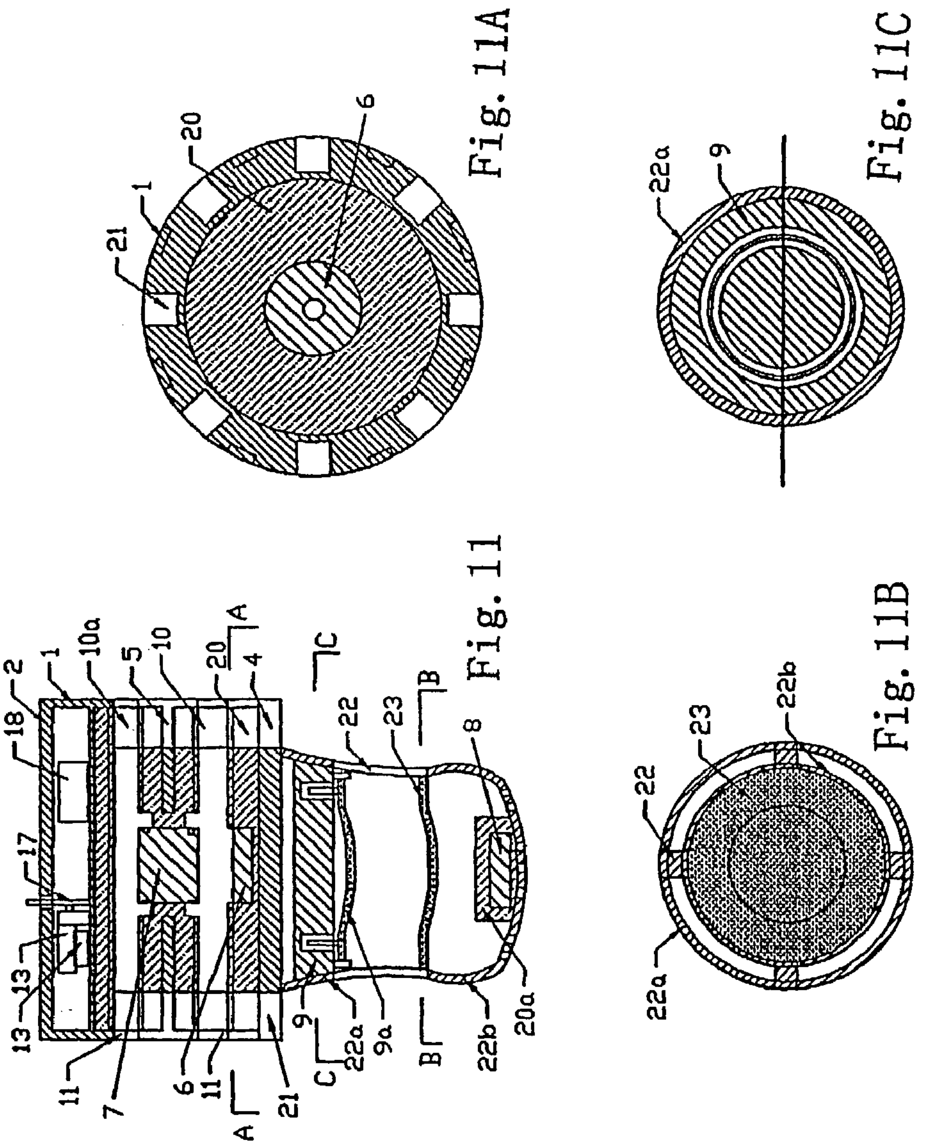
FIG. 11 is a sectional view of the tenth embodiment of an open-style active suppressing receiver.
FIG. 11A~FIG. 11C are the sectional views along the lines of A—A, B—B and C—C shown in FIG. 11 respectively.
Figure 12A:
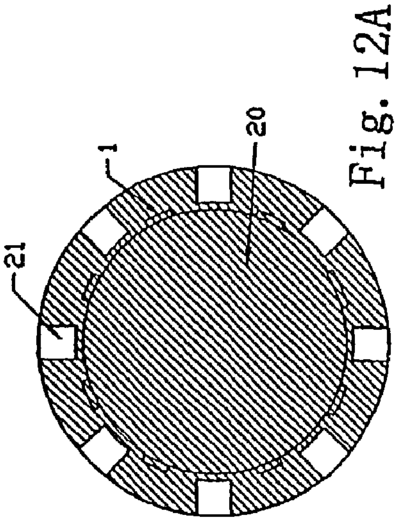
FIG. 12A~FIG. 12C are the sectional views along the lines of A—A, B—B and C—C shown in FIG. 12 respectively.
Figure 12B:
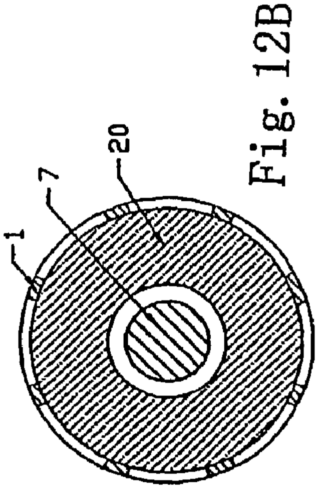
Figure 12:
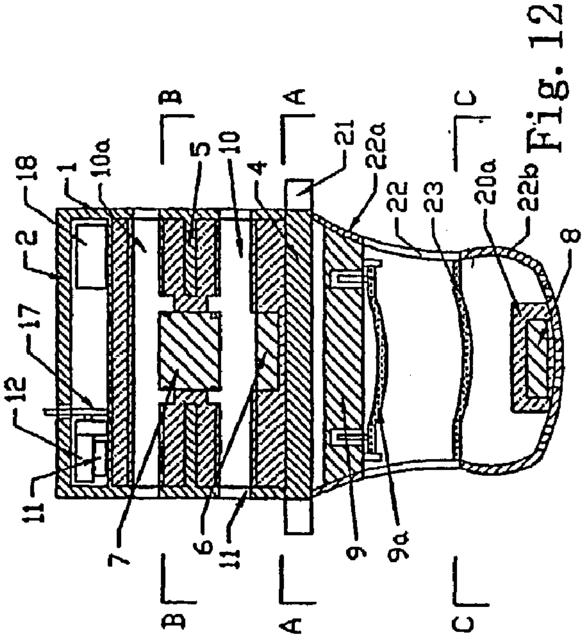
FIG. 12 is a sectional view of the eleventh embodiment of an open-style active suppressing receiver.
Figure 12C:
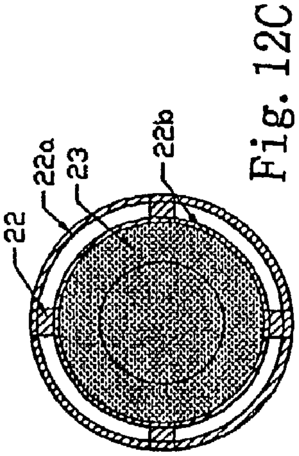

Digital signal processing circuit can perform the digital common mode rejection computer flow chart in FIG. 9 or the digital acoustic noise canceling positioning receiving computer flow chart operation in FIG. 10.

Figure 21A:
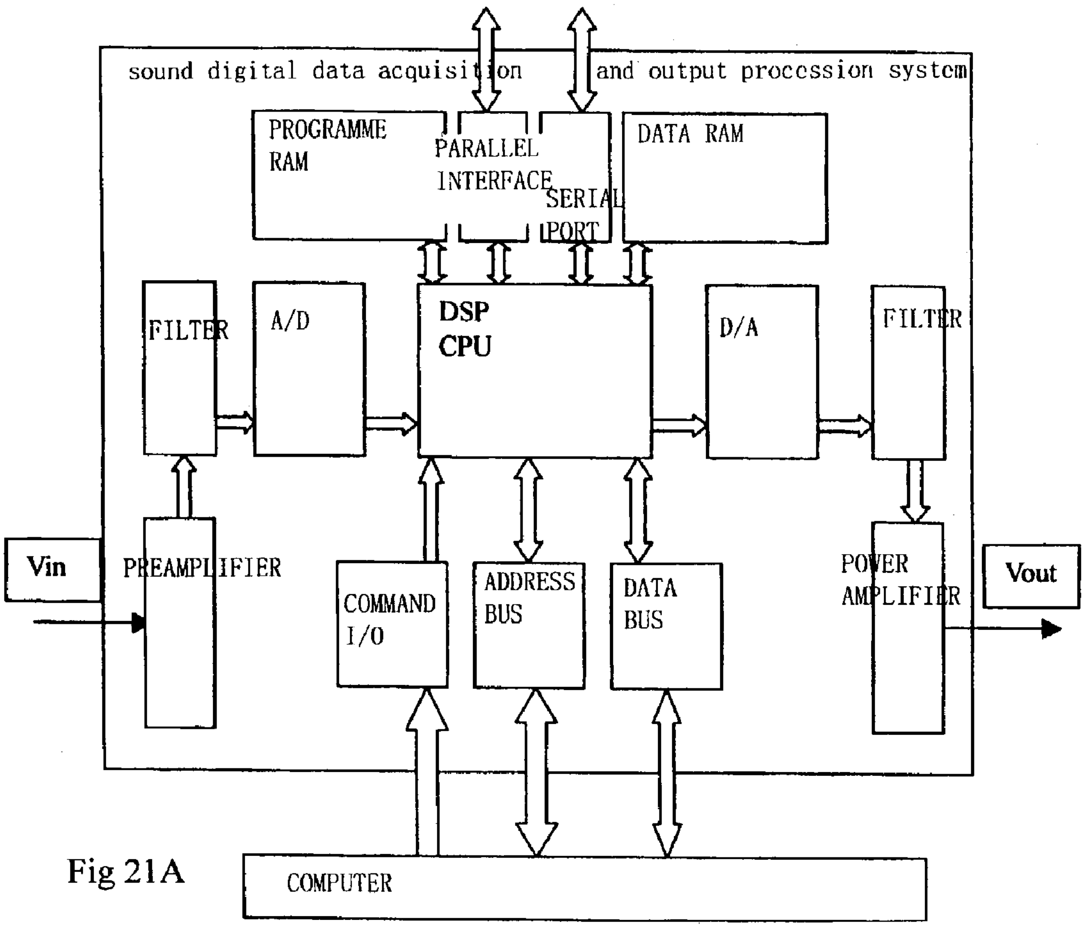
FIG. 21*a* and FIG. 21*b* are the block diagrams of a digital data acquisition common mode rejection system respectively.
Figure 21B:
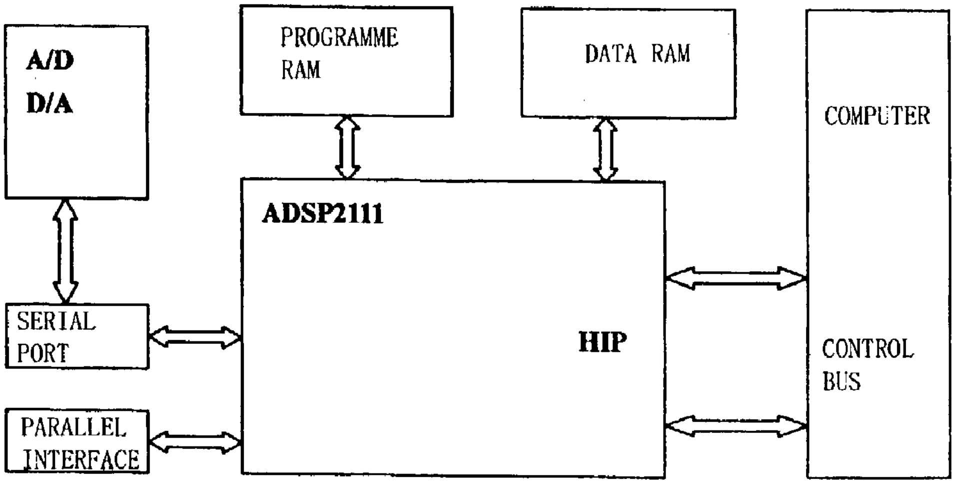

FIGS. 21*a* and 21*b* show the block diagram of a digital data acquisition common mode rejection system circuit, respectively.

FIGS. 21*a* and 21*b* is a further description of the common mode signal rejection and positioning receiving system circuit described in FIG. 6*d*, namely, digital common mode rejection and positioning receiving system circuit, namely, the circuit diagram of a digital data acquisition common mode rejection and positioning receiving system circuit used in the pickups of the invention.

FIG. 21*a* describes the circuit diagram of a digital data acquisition common mode rejection and positioning receiving system circuit used in the pickups of the invention.

In this embodiment: Sound data acquisition processing output device and computer constitute the parallel processing device of the digital signal processing system of the invention. The sound data acquisition processing output device receives the signals output from the pickup in the pickup of the invention and the signals are then amplified by a preamplifier and receive various filtering preprocesses, converted into digital signals through the analog/digital conversion circuit and input to the central processing unit CPU or digital signal processor DSP. If two pickups are available in a pickup, digital signal common mode rejection processing (or other processing, such as positioning receiving processing) can be performed and then differential mode digital signals can further be processed and its results are exchanged with computer through the address bus and the data bus or output to other equipment through parallel interfaces or serial interfaces. Sound digital signals can also be converted into analog signals through the digital and analog converter, then filtered for power amplification output. The computer can communicate with the sound data acquisition processing output device through the bus interface, parallel or serial interface to transmit instructions or receive data. Since the sound data acquisition processing output device has a program memory and data memory, the central processing unit CPU or the digital signal processor DSP which can run the data acquisition processing program, therefore, it can form an independent working system. Based on needs, we can also use only some part of this system to form an independent system and use only a part in front or some parts in it without using the computer.

If the several pickups of several low noise pickups are used for receiving sound signals, a relevant number of circuits must be available in this sound data acquisition processing output device as the input preamplifier circuit and filtering circuit analog/digital conversion circuit. In this sound data acquisition processing output device, CPU or DSP of any type or digital circuit of any type which can perform this operation can be used based on needs. We can also use 8 bit or above 8 bit analog/digital converter, digital and analog converter, preamplifier, filtering circuit and power amplification circuit. The computer interface circuit, parallel interface and serial interface can also be provided subject to needs.

Here we can use various digital signal processors, the central processing unit CPU and various digital circuits which can perform this operation, as well as various analog/digital conversion circuits and digital and analog conversion circuits.

FIG. 21*b* describes the circuit diagram of a digital data acquisition common mode rejection system used in the pickup of the invention. After the sound signals received by pickups M2 and M1 are input to preamplifier, they pass through the analog/digital conversion circuit AD1847 and CPU (ADSP2111 and other digital processing units) for common mode rejection operation. Then they are output to a computer or other digital signal processing equipment through input/output interface or pass through AD1847 digital and analog conversion circuit to be converted from digital into analog signals and then are output. Here we can use various digital signal processor and CPU and other digital circuit which can perform this operation, as well as various analog/digital conversion circuits, digital/analog conversion circuits, etc.

Figure 22A:
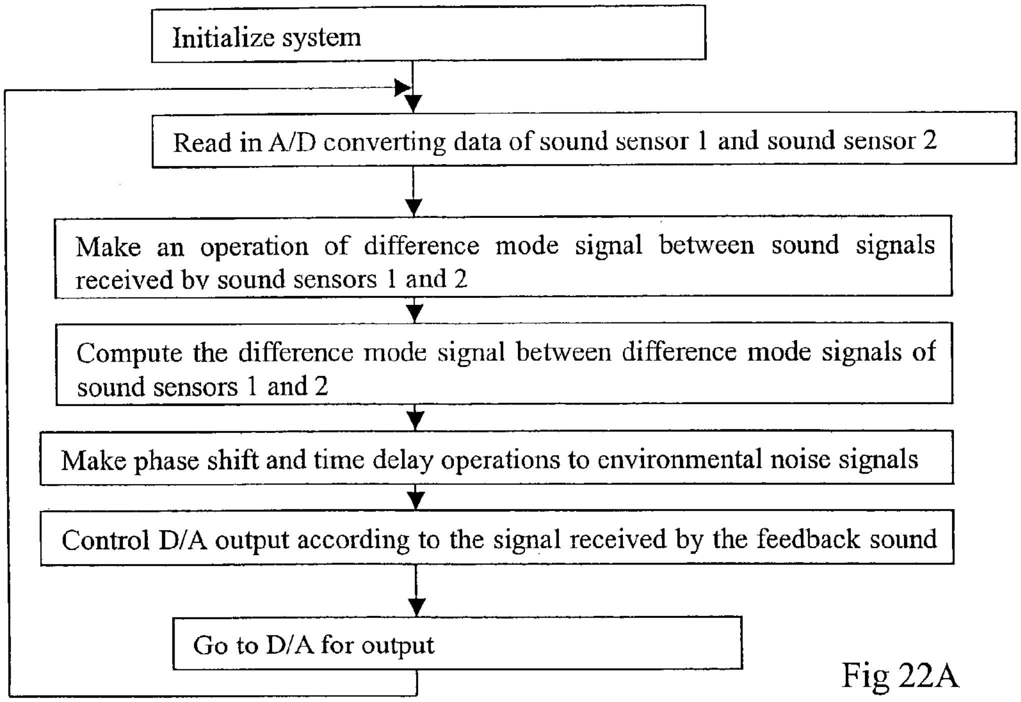
FIGS. 22*a*, 22*b* and 22*c* are the computer flow chart of a digital noise-canceling system respectively according to the invention.

FIG. 22*a* describes a digital common mode rejection computer flow chart used in the pickup of the invention.

We now describe the principle of the digital common mode rejection performed by the pickup in the invention.

When environmental noise pickup 6 is used as a common pickup of the environmental noise pickup and the acoustic noise-canceling pickup, the sound signals received by environmental noise pickup 6 and the sound signals picked up by acoustic noise-canceling pickup 7 will be A/D converted. From them the feedback sound wave electric signals of the sound wave signals output from pickup speaker 9 are collected through common mode rejection. Since the low frequency characteristics of an acoustic noise-canceling pickup differ from its high frequency characteristics, the frequency compensation program can be performed first based on the design requirement and the sound signals received by environmental noise pickup 6 and the sound wave electric signals fed back through common mode rejection perform another common mode rejection to remove the feedback sound wave electric signals of the sound wave signals output from speaker 9 and received by environmental noise pickup 6 to eliminate the feedback noises due to the negative feedback of sound waves caused by the use of "open-style sound wave entrance channel" to obtain clean environmental noise signals. The phase of the signals is shifted and delayed for further processing. Based on the size of the offset environmental noise signals picked up by the feedback pickup, adjustment is made to offset the output signals of environmental noises that enter the ear through D/A output and environmental noise signal phase difference 180°. They are then output from D/A.

If only the environmental noise pickup 6 is used and the acoustic noise-canceling pickup 7 is not used based on the embodiment in FIG. 2, it is possible not to run the common mode rejection program.

Figure 22B:
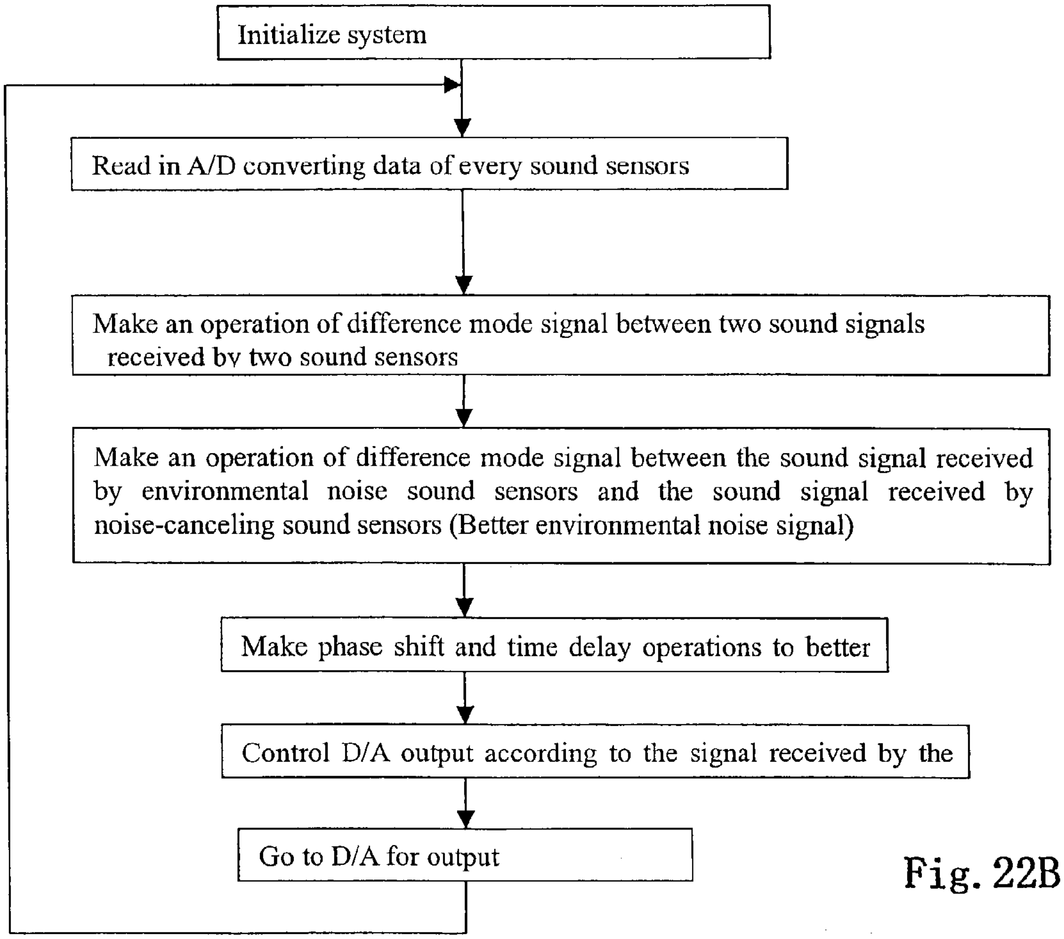

FIG. 22*b* describes a digital common mode rejection computer flow chart used in the pickup of the invention.

We now describe the principle of digital common mode rejection of the pickup in the invention.

When a plurality of acoustic noise-canceling pickups 7*a* and 7*b* are used, the sound signals picked up by them will undergo the A/D conversion processing. Common mode rejection is performed to collect the feedback sound wave electric signals of the sound wave signals output from speaker 9. The sound signals received by environmental noise pickup 6 and the feedback sound wave electric signals of the acoustic noise-canceling pickup undergo again the common mode rejection to remove the feedback sound wave electric signals of the sound wave signals output from speaker 9 and received by environmental noise pickup 6 to eliminate the feedback noises due to the negative feedback of sound waves caused by the use of "open-style sound wave entrance channel" to obtain clean environmental noise signals. The phase of the signals is shifted and delayed for further processing. Based on the size of the offset environmental noise signals picked up by the feedback pickup, adjustment is made to offset the output signals of environmental noises that enter the ear through D/A output and environmental noise signal phase difference 180°. They are then output from D/A. Delay program can be employed to delay for a certain time the sound electric signals picked up by the acoustic noise-canceling pickup next to the receiver. Then they undergo the common mode rejection together with the sound electric signals picked up by another acoustic noise-canceling pickup to reduce the problem that the low and high frequency characteristics of the common acoustic noise-canceling pickups are not conform to each other. We can also perform frequency compensation first based on the design requirement and then perform common mode rejection together with the outside environmental noise electric signals received by environmental noise pickup 6. The electric signals can be compensated by amplitude compensator 24 and one or two of the two electric signals can be compensated for the difference in time due to their difference in position through the time delay compensation program. It is also possible not to use time delay program and perform common mode rejection to the two electric signals to remove the feedback sound wave electric signals of the sound wave signals output from speaker 9 and received by environmental noise pickup 6 to eliminate the feedback self-excitation triggered by the feedback of sound waves output from speaker 9.

Figure 22C:
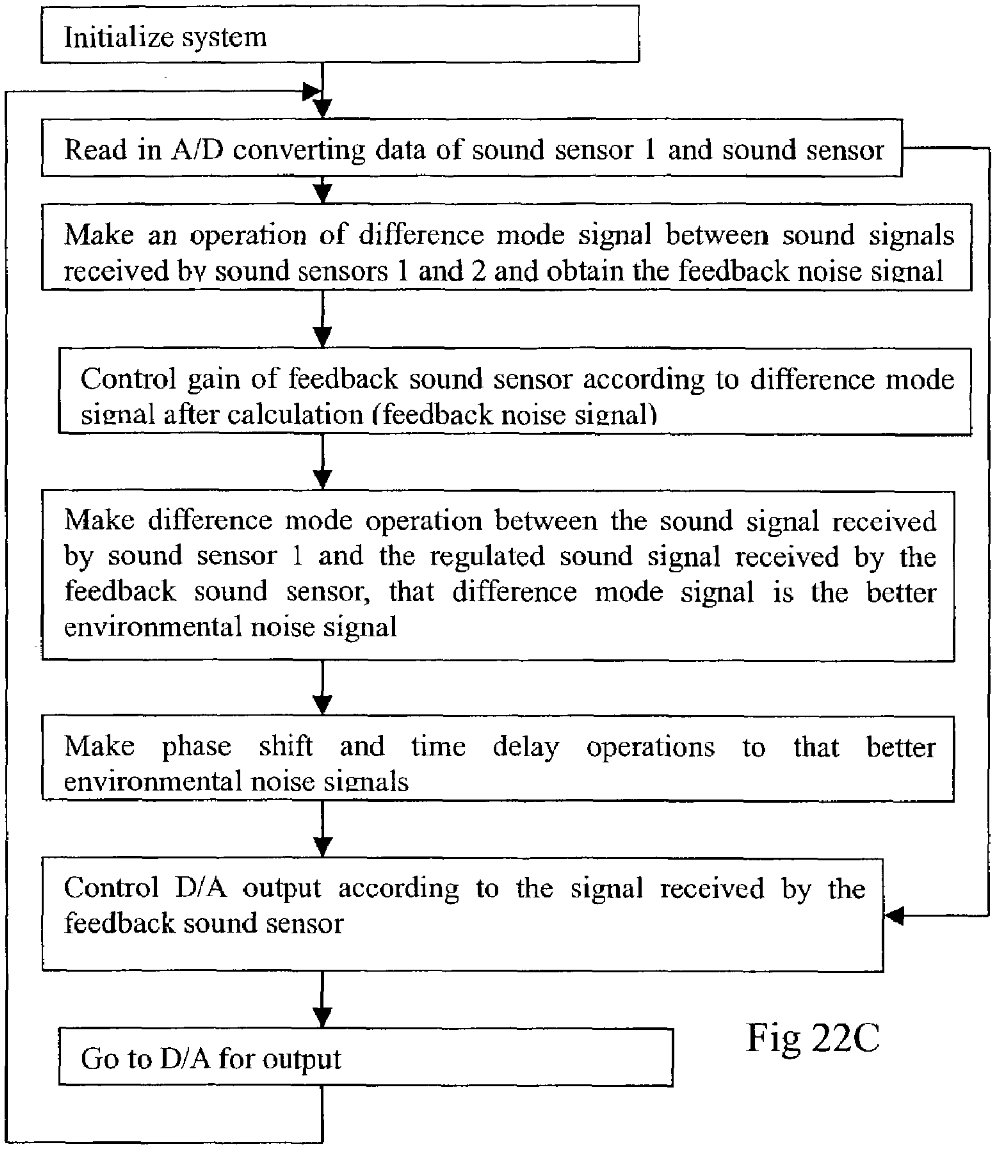

FIG. 22*c* describes a digital common mode rejection computer flow chart used in the pickup of the invention.

We now describe the principle that the digital common mode rejection can be performed by the pickup in the invention.

When environmental noise pickup 6 is used as a common pickup of the environmental noise pickup and the acoustic noise-canceling pickup, the sound signals received by environmental noise pickup 6 and the sound signals picked up by acoustic noise-canceling pickup 7 will be A/D converted. From them the feedback sound wave electric signals of the sound wave signals output from pickup speaker 9 are collected through common mode rejection. Since the low frequency characteristics of an acoustic noise-canceling pickup differ from its high frequency characteristics, the frequency compensation program can be performed first based on the design requirement. The sound signals whose noises have been canceled actively and which are received by the feedback pickup and the effective input signals undergo a series of processes, such as the delay operation, etc, and then the feedback sound wave electric signals collected through the common mode rejection operation and the sound signals received by the feedback pickup are filtered digitally to filter each sound wave in the two paths of sound signals and every the sound waves with the same wave form is found out in each path of sound signals for a comparison of power and the ratio between the two is calculated. This ratio is used to adjust the amplification coefficient of the sound signals received by the feedback pickup so that they and the feedback sound wave electric signals of the sound wave signals output from speaker 9 and received by environmental noise pickup are similar in size. This sound signal and the sound signal received by environmental noise pickup 6 undergo the common mode rejection operation to remove the feedback sound wave electric signals of the sound wave signals output from speaker 9 and received by environmental noise pickup 6 to eliminate the feedback noises due to the negative feedback of sound waves caused by the use of "open-style sound wave entrance channel" to obtain clean environmental noise signals. The phase of the signals is shifted and delayed for further processing. Based on the size of the offset environmental noise signals picked up by the feedback pickup, adjustment is made to offset the output signals of environmental noises that enter the ear through D/A output and environmental noise signal phase difference 180°. They are then output from D/A. We can also use a plurality of noise-canceling pickups 7*a* and 7*b* to A/D convert the sound signals picked up by them. Common mode rejection can performed to collect the feedback sound wave electric signals of the sound wave signals output from speaker 9 or the feedback sound wave electric signals of the sound wave signals output from speaker 9 of an individual acoustic noise-canceling pickup environmental noise pickup.

In the circuits in FIGS. 17 to 21*b* and the computer flow chart in FIGS. 22*a* and 22*c*, if the sound wave signals picked up by the environmental noise pickup and the sound signals output from the near sound source and picked up by the acoustic noise-canceling pickup undergo the common mode rejection operation for eliminating the sound wave electric signals output from the near sound source and picked up by the environmental noise pickup and no further phase shift is performed and instead they will be treated by the output circuit to output the environmental noise signals of the sound wave signals output from the near sound source and received by the environmental noise pickup. In this manner, this circuit together with the noise-collecting module can become an acoustic noise-canceling pickup which, except the sounds output from near sound source, only outputs the sounds output from remote environmental sound sources. The electric signals output from this acoustic noise-canceling pickup can be superimposed on the environmental noise sound electric signals whose phase has been shifted after being treated by electric signal input circuit 28 and compensated of power by output circuit 27 and output to speaker 9 for output. In this way, in the output of speaker 9, the sound waves output from the environmental sound source can be removed from the sound wave electric signals output from near sound source.

Figure 23A:
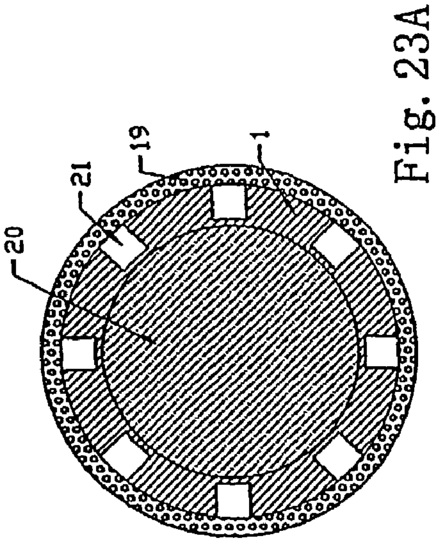
FIG. 23 is a sectional view of an open-style active suppressing receiver and FIG. 23A~FIG. 23C are the sectional view along the lines of A—A, B—B and C—C shown in FIG. 23.
Figure 23C:
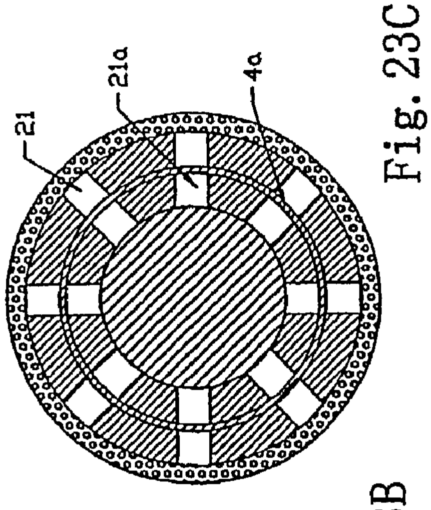
Figure 23:
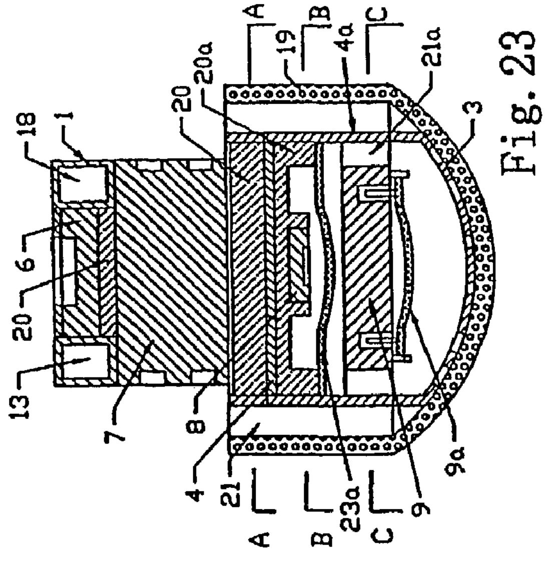
Figure 23B:
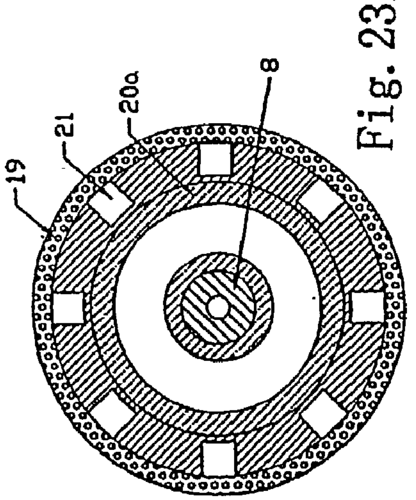

FIG. 23 is the No. 16 embodiment of the invention, the sectional schematic view of the open-style active noise suppressing receiver, and FIGS. 23A to 23C are the sectional view along the lines of A—A, B—B and C—C as shown in FIG. 23.

Figure 24A:
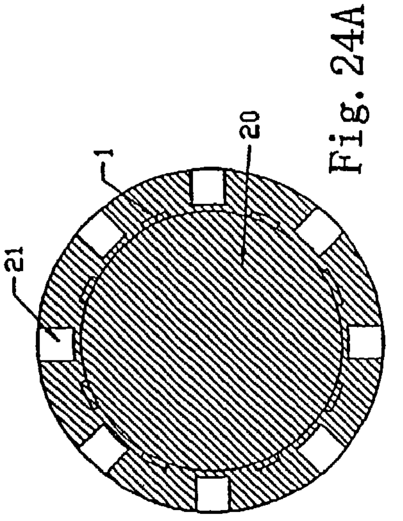
FIG. 24 is a sectional view of an open-style active suppressing receiver and FIG. 24A~FIG. 24C are the sectional view along the lines of A—A, B—B and C—C shown in FIG. 24.
Figure 24B:
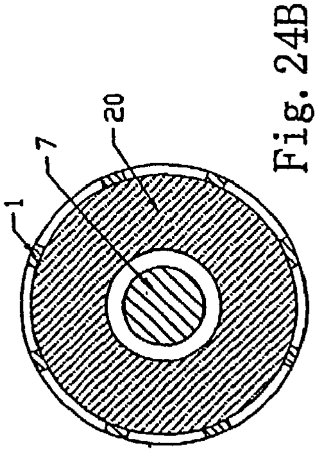
Figure 24:
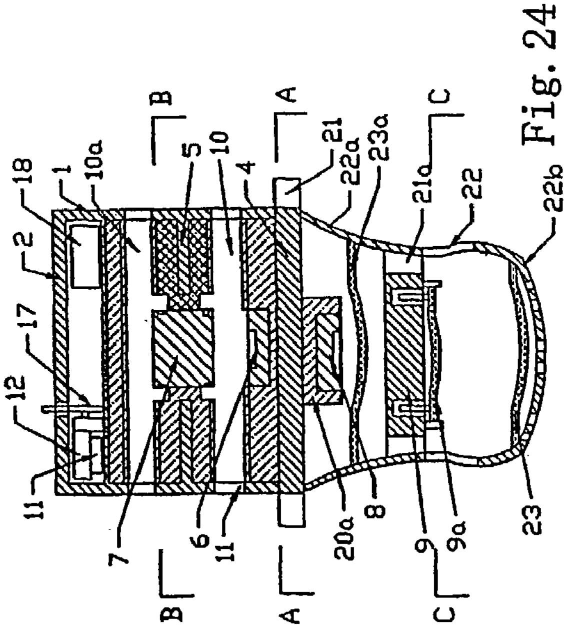
Figure 24C:
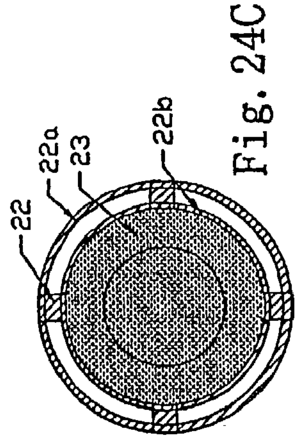

FIG. 24 is the No. 17 embodiment of the invention, the sectional schematic view of the open-style active noise suppressing receiver, and FIGS. 24A to 24C are the sectional view along the lines of A—A, B—B and C—C as shown in FIG. 24.

Refer to FIGS. 23, 23A, 23B and 23C. We can see that acoustically transparent diaphragm 23*a* placed behind the receiver 9 and feedback pickup 8 fixed by sound-proof anti-vibration pad 20*a* behind transparent diaphragm 23*a* are added on the basis of FIG. 8. An acoustic channel 21 a can be found between receiver 9 and the cylinder internal wall 4*a*. In the environmental noise-collecting module, a noise-canceling pickup 7 can be used directly on cylinder 1 and environmental noise collection pickup 6 is placed in the internal side of front cover 2. Environmental noise-collecting cavity and environmental noise-collecting cavity entrance are removed. Printed circuit board and circuits 13 on it are available. Working circuits communicate with outside circuits through lead-out wire, infrared receiving-transmitting device and antenna. Volume adjuster is connected in working circuit 13 to control the volume of this open-style active noise suppressing receiver. Working circuit 13 is provided with power by battery 18.

Refer to FIGS. 24, 24A, 24B and 24C. We can see that acoustically transparent diaphragm 23*a* placed behind the receiver 9 and feedback pickup 8 fixed by sound-proof anti-vibration pad 20*a* behind the transparent diaphragm 23*a* are added on the basis of FIG. 12. An acoustic channel 21*a* can be found between the speaker 9 and the cylinder internal wall 22.

Figure 25:
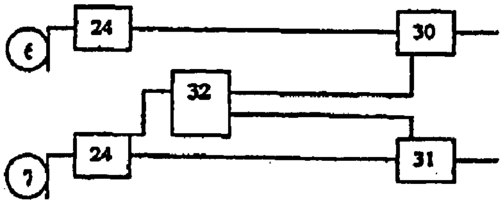
FIG. 25 is a block diagram illustrating a sound signal control switch circuit used in an open-style active noise-suppressing receiver according to the invention.

FIG. 25 shows the circuit block diagram of the sound signal control switch of an open-style active noise suppressing receiver of the invention.

Refer to FIG. 25. When the sound wave signals of the sound wave signals output from the near sound source and picked up by the individual acoustic noise-canceling pickup 7 invented by me and provided in the above patent and patent application technical schemes, amplitude compensator 24 performs amplitude compensation. The environmental noise pickup 6 receives the sound wave electric signals output from the outside environmental sound source and amplitude compensator 24 performs amplitude compensation. The sound signals output from near sound source and received by the acoustic noise-canceling pickup are used, which then pass through the comparator circuit and program 32. If the voltage of the sound signals output from the near sound source and received by acoustic noise-canceling pickup is above the designated voltage (lower limit of the designed distance), switch 31 will be activated to output sound signals output from the near sound source and received by acoustic noise-canceling pickup, when switch 30 is shut down. If the voltage of the sound signals output from the near sound source received by acoustic noise-canceling pickup is below the designated voltage, switch 30 will be activated to output sound signals output from signals received by acoustic noise-canceling pickup, when switch 31 is shut down.

Figure 26A:
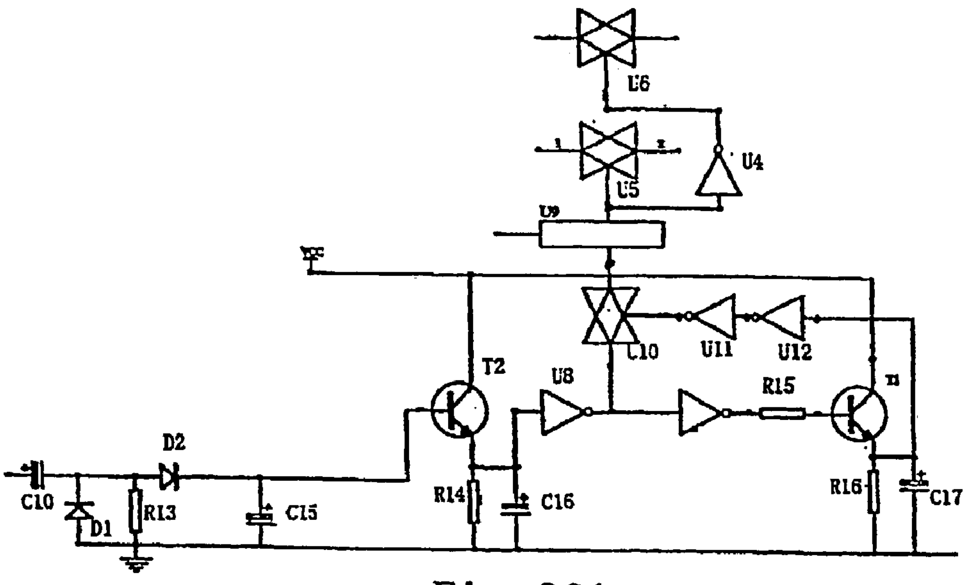
FIG. 26*a* and FIG. 26*b* are the circuit diagram of the sound signal control switch of an open-style active noise-suppressing receiver according to the invention.
Figure 26B:
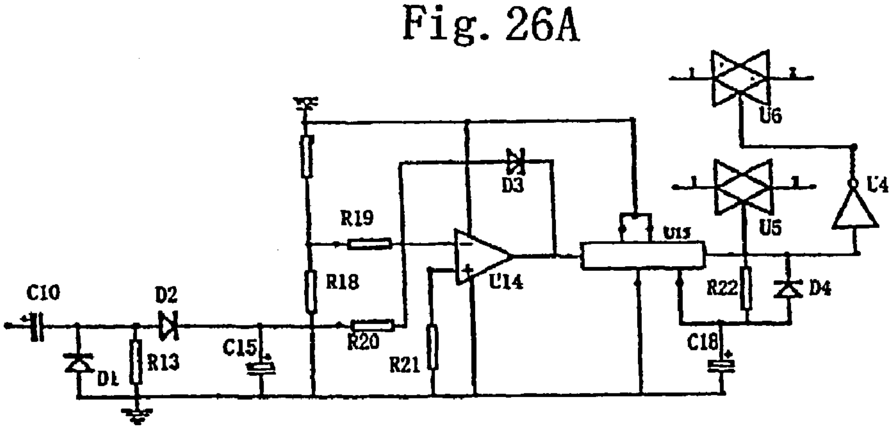

FIGS. 26*a* and 26*b* shows the circuit block diagram of the sound signal control switch of an open-style active noise suppressing receiver of the invention.

Refer to FIG. 26. A sound control switch circuit as shown in FIG. 24*a* is provided between capacitor C10 and NOT gate U4, analog switches U6, U5. It consists of: The low distortion and low noise sound signals output from the common mode signal rejection circuit pass through capacitor C10 and the detecting circuit consisting of diodes D1, D2 and resistor R9 and the sound control switch circuit consisting of triode T2, capacitors C15, C16 and C17 and resistors R14, R15 and R16 and NOT gates U8, U13, U11 and U12, analog switch U10 and R-J trigger U9 to control the control end 13 of analog switch U5 so that it is on. Sound signals inputted from input end 1 are output from output terminal 2 and pass through the opposite direction of NOT gate U4 to control the control end 13 of analog switch U6 so that it is off. Sound signals inputted from input end 1 cannot be output from output terminal 2. For the analog switches U5 and U6, one is on, the other is off. On the contrary, when the sound signals output from sound source are not inputted, the 'on' and 'off' will be reversed. Arrangement of capacitor C17 and R16 can decide the on and off time of analog switch U5 and U6 after a talk is finished (such as after 10 seconds) to prevent a short time interruption during talk from turning U5 and U6 on and off in a wrong manner. The 'on' and 'off' of analog switches U5 and U6 can decide which path of sound signals to be output which are inputted from the input end of U5 and U6 and picked up by environmental noise pickup and acoustic noise pickup.

Refer to FIG. 26*b*. A sound control switch circuit as shown in FIG. 24*b* is provided between capacitor C10 and U4, U6 and U5. Its principle is the same as that in embodiment 24*a*, only that the sound control circuit for controlling the analog switch uses a comparator circuit. We now make a description of the comparator circuit: It consists of: The low distortion and low noise sound signals output from common mode signal rejection circuit pass through capacitor C10 and the detecting circuit consisting of diodes D1 and D2 and the sound control switch circuit consisting of resistors R17, R18, R19, R20 and R21, voltage-regulation diode D3, diode D4, capacitors C15 and C18, arbitrary level comparator U14 and R-J trigger U15 to control the control end 13 of analog switch U5 so that it is on. Sound signals inputted from input end 1 are output from output terminal 2 and pass through the opposite direction of NOT gate U4 to control the control end 13 of analog switch U6 so that it is off. Sound signals inputted from input end 1 cannot be output from output terminal 2. For the analog switches U5 and U6, one is on, the other is off. On the contrary, when the sound signals output from sound source are not inputted, the 'on' and 'off' will be reversed. Arrangement of capacitor C18 and R22 can decide the on and off time of analog switch U5 and U6 after a talk is finished (such as after 10 seconds) to prevent a short time interruption during talk from turning U5 and U6 on and off in a wrong manner. The 'on' and 'off' of analog switches U5 and U6 can decide which path of sound signals to be output which are inputted from the input end of U5 and U6 and picked up by environmental noise pickup and acoustic noise pickup.

All the circuits in the signal control switch circuit used in FIGS. 24*a* to 24*b* can use integrated circuits or discrete component circuits, as well as comparator circuit and trigger circuit of any type. Subject to needs, analog circuit, digital circuit and running program needed or the combination of the two can be used, as well as circuits of all types which can complete the functions of the entire circuit.

Figure 27:
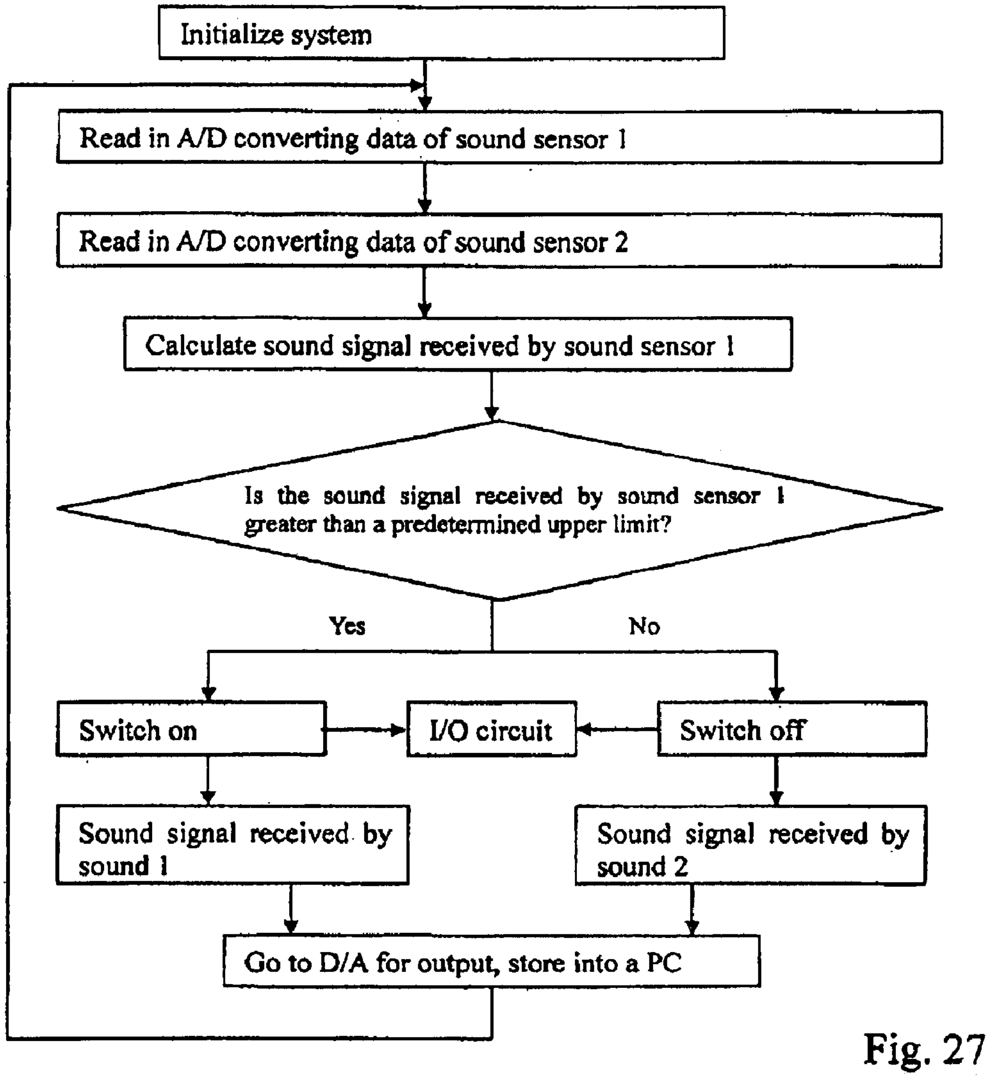
FIG. 27 is a computer flow chart of a sound signal control switch used in an open-style active suppressing receiver according to the invention.

FIG. 27 describes the computer flow process of a sound signal control switch used in the open-style active noise suppressing receiver in the invention.

We now describe the principle that the pickup in the invention can perform the sound signal control switch. The sound signals output from near sound sources and received by acoustic noise-canceling pickup and the sound signals output from environmental sound source and received by the environmental noise pickup are used and analog/digital conversion circuit is used to convert analog signals into digital ones. Acoustic noise-canceling pickup is used to receive sound signals output from near sound sources. This circuit and program are in fact a comparator program. If the voltage of the sound signals output from the near sound source and received by acoustic noise-canceling pickup is above the designated voltage (low limit of the designed distance), then switch program is activated to output the sound signals output from the near sound source and received by acoustic noise-canceling pickup to digital/analog converter or computer to control input/output circuit (I/O circuit) to output on or off signals at the same time. If the voltage of the sound signals output from the near sound source and received by the acoustic noise-canceling pickup is below the designated one, the switch program will be turned off to output the signals received by environmental noise pickup to digital/analog converter or control input/output circuit (I/O circuit) to output on or off signals at the same time.

Figure 28:
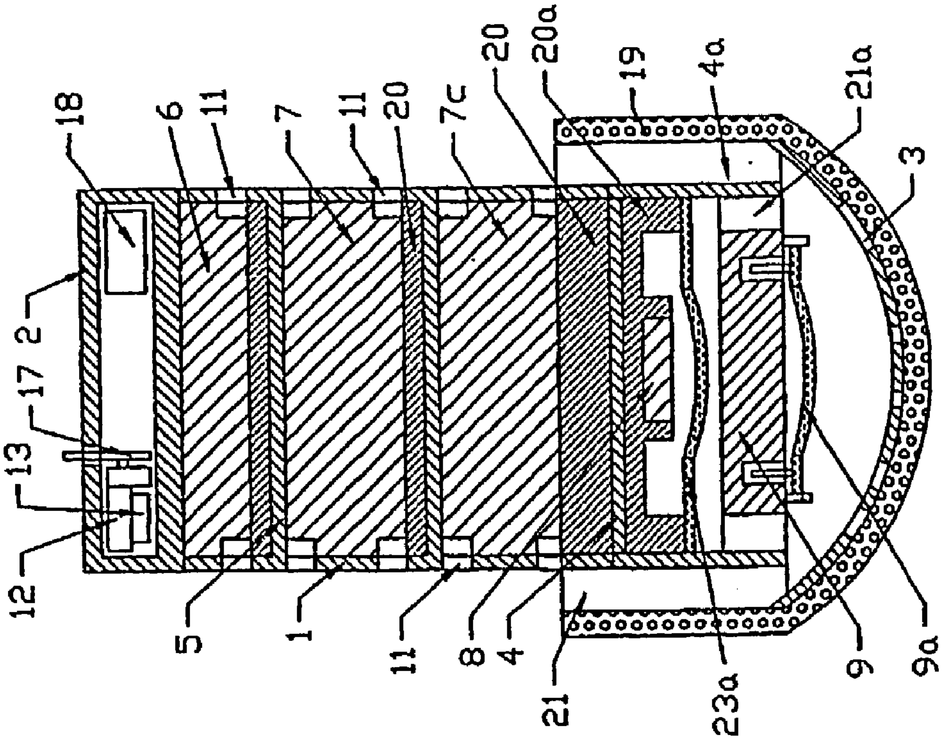
FIG. 28 is a sectional schematic view of an open-style active suppressing receiver according to the invention.

FIG. 28 is the sectional schematic view of an open-style active noise suppressing receiver in the invention.

Compared with FIGS. 3 and 23, we can see that their difference lies in: In the noise-collecting module, acoustic noise-canceling pickup 7 and 7C and environmental noise pickup 6 are placed inside cylinder 1, in which the. acoustic noise-canceling pickup 7 and 7C and environmental noise pickup 6 use the acoustic noise-canceling pickup and non-acoustic noise-canceling pickup with their inlet holes opening on the sidewall of cylinder involved in the several previous inventions of the inventor. Of course we can also use the acoustic noise-canceling pickup and non-acoustic noise-canceling pickup used in the each previous embodiment according to the design requirement. In this way, it is possible not to use environmental noise-collecting cavity 10, acoustic noise-canceling pickups 7 and 7C and environmental noise pickup 6 to receive outside environmental noise and the feedback signals of sound wave signals output from the speaker 9. What are output from acoustic noise-canceling pickups 7 and 7C are mainly the feedback signals of sound wave signals output from speaker 9 and a few sound wave electric signals of environmental noises. We can use the circuit in the digital data collection common mode rejection system circuit block diagram in FIG. 21*a* and/or FIG. 21*b* and a digital noise canceling computer flow in FIG. 32 to determine the feedback signals of the sound wave signals output from speaker 9 in various methods and then pass through the common mode rejection circuit with the sound wave electric signals received by environmental noise pickup 6 to remove the feedback sound wave electric signals of the sound wave signals received by environmental noise pickup 6 and output from speaker 9 to eliminate the feedback noises due to the negative feedback of sound waves caused by use of the "open-style sound wave entrance channel". The environmental noise pickup 6 uses a non-acoustic noise-canceling pickup whose inlet hole is opened on the sidewall of cylinder. It can also use other types of non-acoustic noise-canceling pickups.

The relative positions between non-acoustic noise-canceling pickups 7 and 7*c* and environmental noise pickup 6 can be exchanged based on the design requirement.

Screen 3 is combined with the external wall of acoustic channel 21, rather than with the internal wall 4*a*. An acoustic channel 21*a* is available between the receiver 9 and the internal wall 4*a*.

Figure 29:
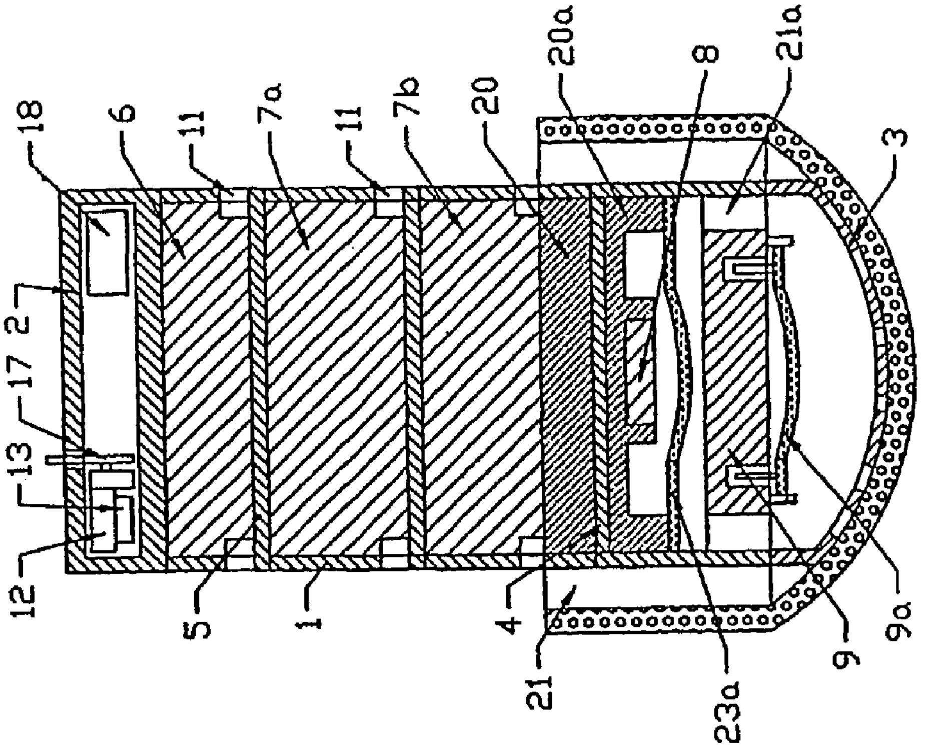
FIG. 29 is a sectional schematic view of an open-style active suppressing receiver according to the invention.

FIG. 29 is the sectional schematic view of an open-style active noise suppressing receiver in the invention.

Compared with FIGS. 2 and 28, we can see that their difference lies in: Acoustic noise-canceling pickups 7 and 7*c* are changed into non-acoustic noise-canceling pickups 7*a* and 7*b* whose structure is basically the same as environmental noise pickup 6, in which inlet holes of non-acoustic noise-canceling pickups 7*a* and 7*b* are opened on the sidewall of cylinder. Other types of non-acoustic noise-canceling pickups can also be used.

Screen 3 is not combined with the external wall of acoustic channel 21, but with the internal wall 4*a*. An acoustic channel 21*a* is available between the receiver 9 and the internal wall 4*a*.

Figure 30:
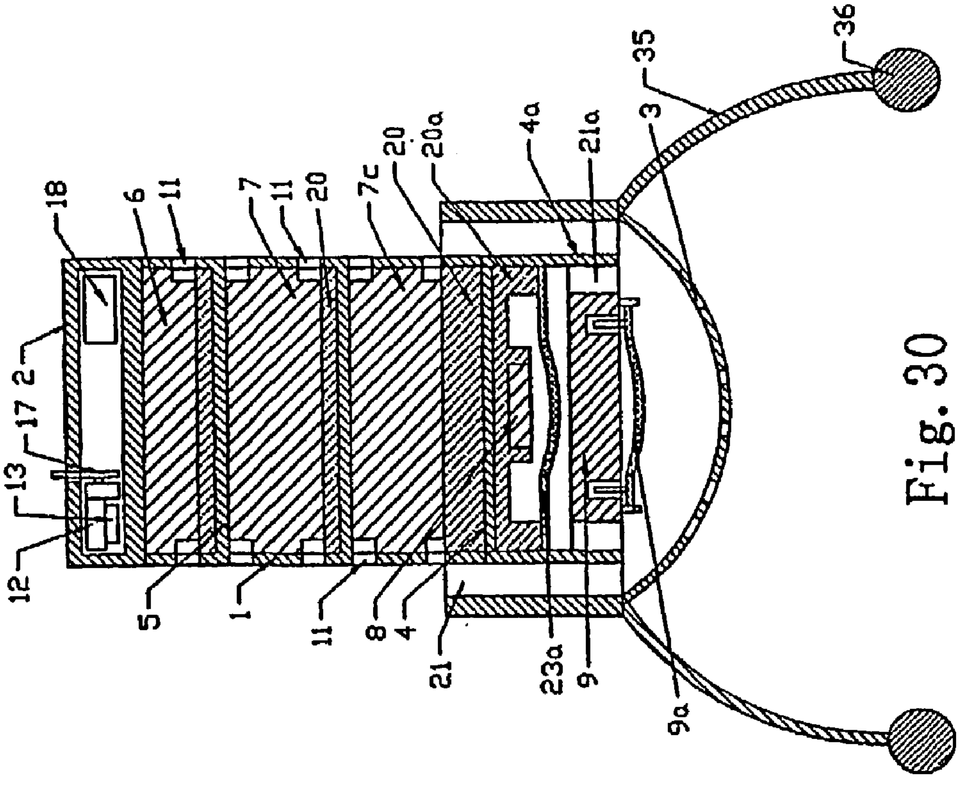
FIG. 30 is a sectional schematic view of an open-style active suppressing receiver according to the invention.

FIG. 30 is the sectional schematic view of an open-style active noise suppressing receiver in the invention.

Compared with FIGS. 28 and 15, we can see that their difference lies in: the noise-collecting module in FIG. 15 is changed into the noise-collecting module in FIG. 28.

Figure 31:
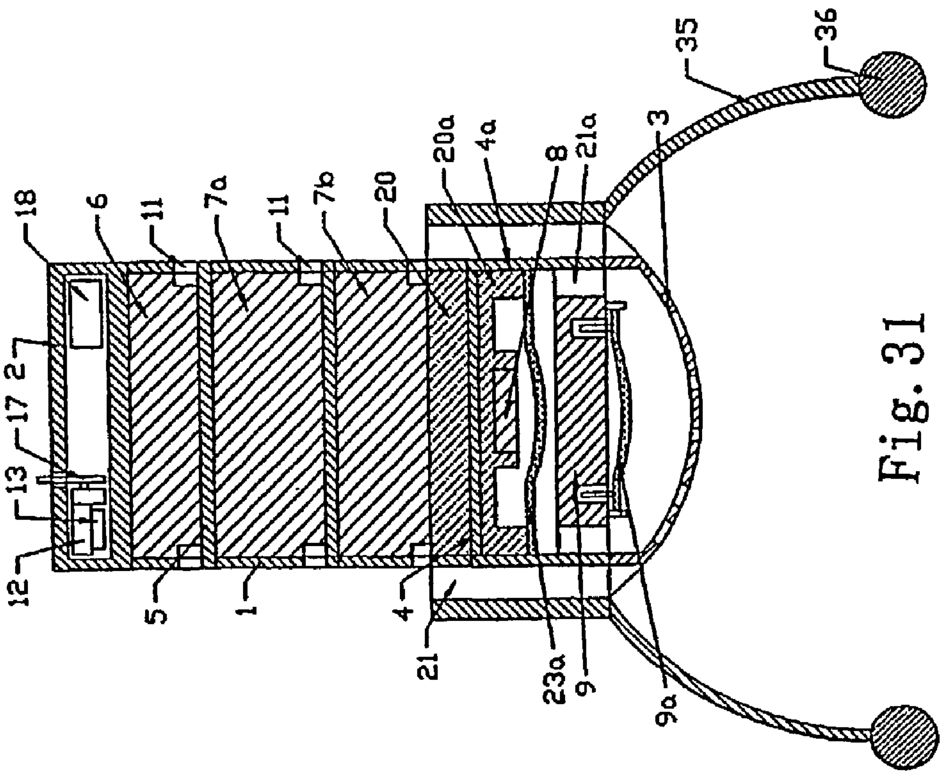
FIG. 31 is a sectional schematic view of an open-style active suppressing receiver according to the invention.

FIG. 31 is the sectional schematic view of an open-style active noise suppressing receiver in the invention.

Compared with FIGS. 28, 29 and 15, we can see that their difference lies in: the noise-collecting module in FIG. 15 is changed into the noise-collecting module in FIG. 29.

Figure 32:
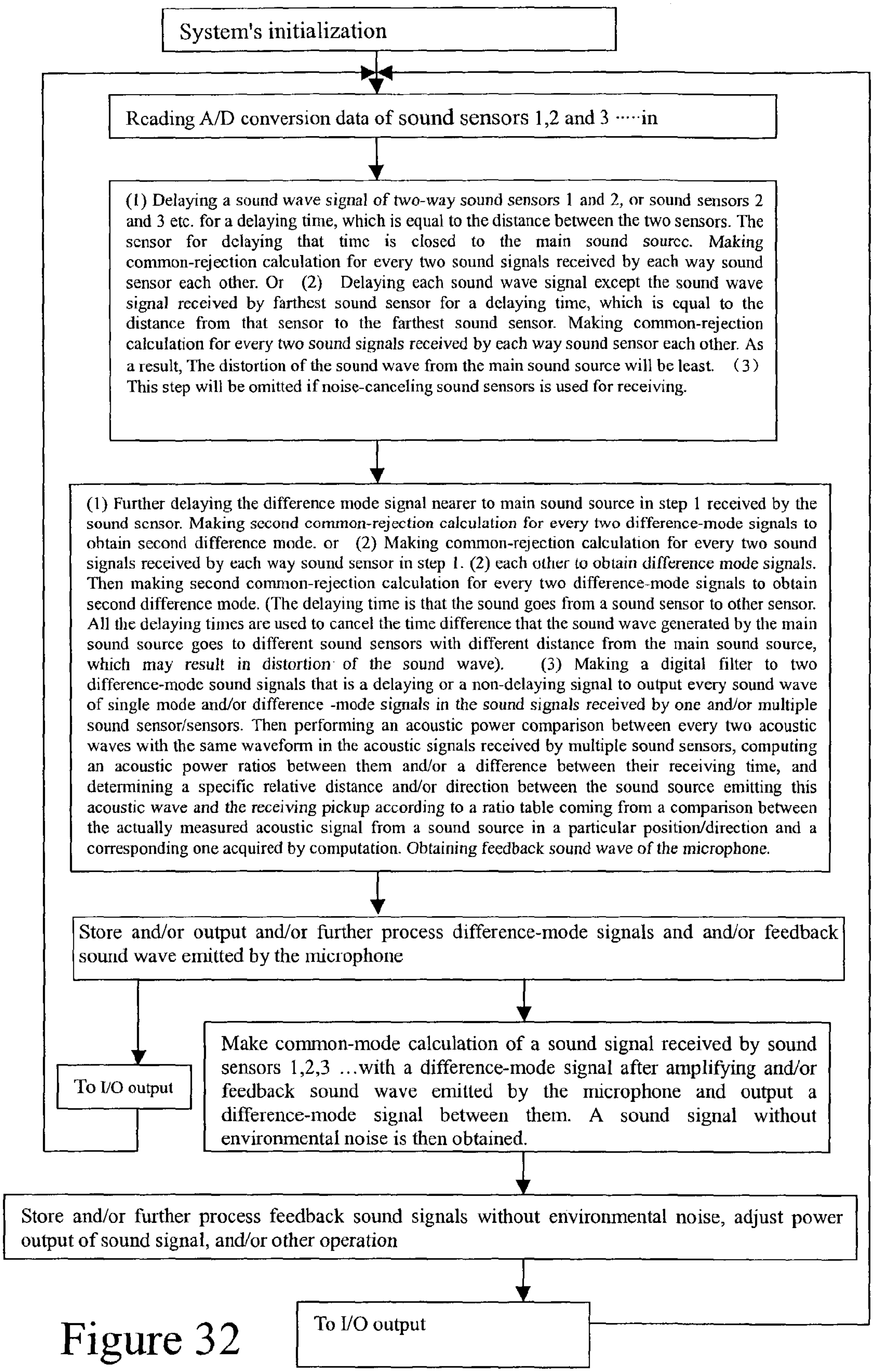
FIG. 32 is the computer flow chart of a digital-noise-canceling used in an open-style active suppressing receiver according to the invention.

FIG. 32 shows a digital noise canceling computer flow used in the open-style active noise suppressing receiver of the invention.

The processing procedure of the invention by use of several two-dimensional structures and/or three-dimensional structure of the acoustic noise-canceling pickups or non-acoustic noise-canceling pickups arranged in order is:

When several non-acoustic noise-canceling pickups are used to receive the sound signals output from the main sound source and/or several acoustic noise-canceling pickups and non-acoustic noise-canceling pickups are used to receive the sound signals output from main sound source, the circuit of the digital data collection common mode rejection system circuit block diagram in FIG. 21*a* and/or 21*b* can be used. First, the sound wave electric signals received by the various pickups are converted by the A/D conversion circuit. Then, the following computer flow can be used:

1. A. When noise receiving modules of noise-suppressing receivers of several two-dimensional structures and/or three-dimensional structure of the non-acoustic noise-canceling pickups arranged in order are used, (1) The path of sound signals of the pickup next to the main sound source in the every two path signals picked up by pickups, such as pickups 1, 2 and pickups 2, 3 . . . , are delayed and the delay time is the time of the sound wave signal transmitted from one pickup to the other. Sound wave signals picked up by every path of pickups undergo the common mode rejection calculation two by two; (2) Or all the sound wave signals picked up by pickups 1, 2 and 3 . . . except the path of signals picked up by pickup which is the farthest to the main sound source, are delayed and time of delay is the time of the sound wave signal transmitted respectively from each pickup near the main sound source to the pickup which is the farthest to the main sound source. After every path of the sound wave signals picked up by those pickups undergo the common mode rejection calculation two by two, then, in differential mode signals, the degree of the distortion of the sound waves output from the main sound source can be minimized. (3) The sound wave signals picked up by all pickups undergo common mode calculation directly two by two. B. When noise receiving modules of noise-suppressing receivers of several two-dimensional structures and/or three-dimensional structure of the acoustic noise-canceling pickups and non-acoustic noise-canceling pickups arranged in order are used, since the sound wave signals received by the acoustic noise-canceling pickup are differential mode signals, the common mode rejection computer flow may not be used.

2. (1) The differential mode signals picked up by the pickup close to the main sound source in multiple paths of differential mode signals obtained in above step 1 are delayed again. We can perform the secondary common mode rejection calculation on the two paths of differential mode signals to obtain differential mode signals again. Or (2) Two or several paths of the differential mode signals obtained in the above step 2, namely, the sound wave signals picked up by each path of pickups undergo the common mode rejection calculation again to obtain differential mode signals again. (the delay time is the time of the sound wave signal transmitted from one pickup to the other. All time delays are intended for eliminating the time difference between two paths of signals which is caused by the sound wave transmission speed of sound waves output from the main sound source when they reach the front and rear pickups. The time difference will cause distortion of sound waves output from the main sound source in differential mode signals caused by the common mode rejection operation). or (3) Two paths of differential mode signals which have or have not been delayed are filtered by digital filtering or other methods to obtain each sound wave in sound signals and/or differential mode signals received by each of the pickup among a plurality of pickups respectively.

3. Then, every sound waves with the same wave form in the sound signals received by a plurality of pickups can be compared of their sound power to calculate the ratio between every sound wave electric signals with the same wave form, and/or the difference between receiving time and other parameters. Based on the distance and/or location relations between a plurality of pickups and the ratio list of sound signals output from the sound source at a certain distance which are actually measured or calculated, we can know the actual distance and/or location of the sound source of the sound wave and the pickup. We can also use any other calculation method to obtain the actual distance and/or location of the sound source which outputs the sound wave and the pickup. At that time, sound wave signals output from the sound source within a certain distance from pickup can be collected, as well as the feedback sound waves of the sound signals output from the microphone.

4. The compensation calculation can be performed on the attenuation of the feedback sound wave signals at different distances which is caused by the difference in the distance of sound source when the acoustic noise-canceling pickup is picking up sound signals (Or a sound wave signals within a certain distance is multiplied by the different amplification coefficient based on the different distance). Common mode calculation is performed between one path of sound wave signals picked up by pickups 1, 2, 3 . . . , the differential mode signals obtained again after amplification and the feedback sound wave signals of the sound signals which have been collected and output from the microphone for which compensation calculation has been made to obtain environmental noise signals in which the feedback sound waves of the sound signals output from the microphone have been eliminated.

5. Environmental noise electric signals obtained in which the feedback sound waves of the sound signals output from the microphone have been eliminated can be stored and/or phase shift and/or sound wave signal power adjustment can be performed so that the sound wave signals input through I/O circuit and output from the receiver as well as the environmental noises that enter external auditory meatus can be offset to each other to substantially eliminate environmental noises. And/or other processes can be performed.

This computer flow can not only use a digital circuit but also use an analog circuit or the combination of the two.

Figure 33:
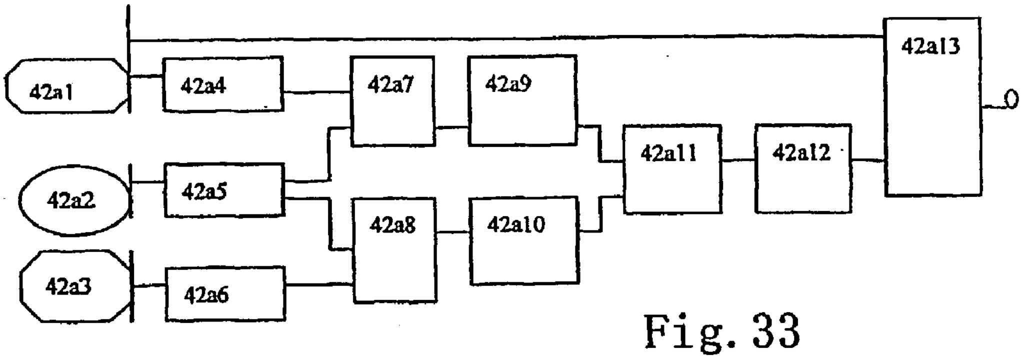
FIG. 33 is a noise-suppressing circuit block diagram used for an open-style active suppressing receiver according to the invention.

FIG. 33 shows an acoustic noise canceling circuit block diagram used in an open-style active acoustic noise suppressing receiver in the invention.

The following is the processing block diagram for performing acoustic noise canceling reception by use of a plurality of two-dimensional structure of the acoustic noise-canceling pickups or non-acoustic noise-canceling pickups arranged in order: when a plurality of non-acoustic noise-canceling pickups 42*a*1, 42*a*2 and 42*a*3 are used to receive the sound signals output from the main sound source, 1.2. can be adopted or the paths of sound wave signals of pickups 42*a*1, 42*a*2 and 42*a*3 (except the path of sound wave signals picked up by the pickup which is the farthest from the main sound source) can pass through time delay circuits 42*a*4, 42*a*5 and 42*a*6. The delay time is the time of the sound wave signal transmitted respectively from each pickup near the main sound source to the pickup which is the farthest to the main sound source. Let the sound wave signals picked up by various paths of pickups to pass through common mode rejection circuits 42*a*7 and 42*a*8 two by two. In this way, the degree of the distortion of the sound waves output from the main sound source in differential mode signals can be minimized. Let the differential mode signals picked up by the pickup near the main sound source in multiple paths of differential mode signals obtained in above step 1 to pass through time delay circuits 42_a_9 and 42_a_10 again and let two paths of differential mode signals pass through the common mode rejection circuit 42_a_11 again to obtain differential mode signals. Or let the two or several paths of the differential mode signals of the paths of differential mode signals obtained in above step 2 after the sound wave signals picked up by pickups undergo the common mode rejection calculation two by two to obtain differential mode signals again. (The delay time is the time of the sound wave signal transmitted from one pickup to another pickup. All time delays are intended for eliminating the time difference between two paths of signals which is caused by the sound wave transmission speed of sound waves output from the main sound source when they reach the front and rear pickups. The time difference will cause distortion of sound waves output from main sound source in differential mode signals caused during the common mode rejection). The differential mode signals obtained again are output and/or processed further. For instance, let one path of the sound wave signals picked up by pickups 42_a_1, 42_a_2 and 42_a_3 and the differential mode signals obtained again after amplification circuit 42_a_12 to pass through the common mode rejection circuit 42_a_13 to obtain differential mode signals between them, so as to obtain environmental noises in which the sound waves output from the main sound source have been eliminated.

We can also replace the common mode rejection circuit 42_a_11 by the circuit in the digital data collection common mode rejection system circuit block diagram in FIG. 21_a_ and/or FIG. 21_b_. Through the digital acoustic noise canceling computer flow in FIG. 41, two paths of differential mode signals which have or have not been delayed are filtered by the means of the digital filtering or other methods, to obtain the sound signals and/or each sound wave in differential mode signals received by each pickup among several pickups respectively. Then, every sound waves with the same wave form in the sound signals received by a plurality of pickups can be compared of their sound power to calculate the ratio between every sound wave electric signals with the same wave form, and/or the difference between receiving time and other parameters. Based on the distance and/or location relations between a plurality of pickups and the ratio list of sound signals output from the sound source at a certain distance which are actually measured or calculated, we can know the actual distance and/or location of the sound source of the sound wave and the pickup. We can also use any other calculation method to obtain the actual distance and/or location of the sound source which outputs the sound wave and the pickup. At that time, sound wave signals output from the sound source within a certain distance from pickup can be collected, as well as the feedback sound waves of the sound signals output from the microphone. The common mode rejection calculation is performed between the sound waves of the feedback signals of the sound signals output from the microphone and the sound electric signals received by the environmental noise pickup to obtain environmental noise electric signals in which the feedback sound waves of the sound signals output from microphone have been eliminated. The environmental noise electric signals obtained in which the feedback sound waves of the sound signals output from the microphone have been eliminated can be stored and/or phase shift and/or sound wave signal power adjustment can be performed, so that the sound wave signals input to the receiver through I/O circuit and then output as well as the environmental noises that enter external auditory meatus can be offset to each other, to substantially eliminate environmental noises. And/or other processes can be perform.

This acoustic noise canceling block diagram flow can be realized by use of a digital circuit, an analog circuit or the combination of the two. For instance, the time delay circuit can use an analog time delay circuit, a CCD time delay circuit, a digital time delay circuit . . .

Figure 34:
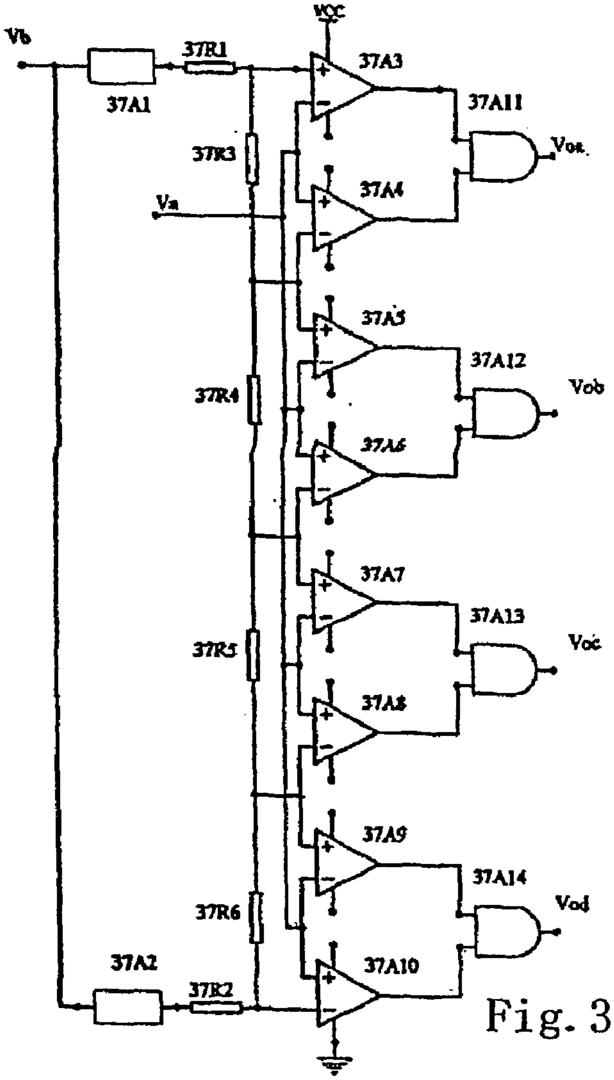
FIG. 34 is a window comparison circuit of multiple sections used for an open-style active suppressing receiver according to the invention, which can adjust the amplifying ratio of amplification circuit according to the receiving distance.

FIG. 34 shows a window comparator circuit with a plurality of intervals (The amplification coefficient of the amplifier can be adjusted based on the receiving distance) used by an open-style active acoustic noise suppressing receiver in the invention.

FIG. 34 uses a window comparator circuit with a plurality of intervals so that the amplifier can select different amplification coefficients based on the distance between the pickup and the sound source.

This is based on this principle, namely, comparison of the ratios between the sound signals output from the main sound source and received by two paths of acoustic noise-canceling pickups to decide the distance between the pickup and the main sound source to figure out the appropriate amplification coefficient of the amplifier at this distance.

In fact, this circuit is a window comparator circuit with a plurality of intervals and gating function. Sound electric signals Va and Vb output from the main sound source and received by two paths of acoustic noise-canceling pickups, assume the sound electric signal output from the main sound source and received by the acoustic noise-canceling pickup next to the sound source is Va and the sound electric signal output from the main sound source and received by the acoustic noise-canceling pickup far from the sound source is Vb, then we can regard them as a reference. Here we assume that Vb is the reference. If the ratio between Va and Vb is between the ratio M to N (M is the ratio of the upper limit when the distance exceeds the designed distance at a certain degree and N is the ratio of lower limit when it is within the designed distance.) Let Vb signals pass through amplification circuits 36A1 and 36A2 for amplification by M and N times (M and N can either be positive or negative, integer or non-integer with decimal). In this way, we can assume that the voltage interval of Vb signal after it passes through amplification circuit 36A1 and 36A2 amplified by M and N times is Vb1, the window comparator circuit with many intervals and gating function has four intervals. Assume 37R3=37R4=37R5=37R6, then when Va is between ¾Vb1 to Vb1, Voa has high level output. When Va is between ½Vb1 to ¾Vb1, Vob has high level output. When Va is between ¼Vb1 to ½Vb1, Voc has high level output. When Va is between 0Vb1 to ¼Vb1, Vod has high level output. Based on the design requirement, Voa, Vob, Voc and Vod high level output can actuate the switches with different amplification coefficients of the analog amplifier respectively, or actuate several alarming circuits respectively, or actuate both the switches with different amplification coefficients of the amplifier and one or more alarming circuits.

For the window comparator circuit with many intervals and gating function, the number of gating intervals and the window voltage values of intervals can be designed based on the design requirement.

Among the circuits in various embodiments of the invention, the comparator circuit can use MC14574 comparator or other comparators and comparator circuits. AND gate circuit can use CD4081 and the said comparator circuit and AND gate circuit can also use other types of comparator circuit, AND gate circuit and NAND gate circuit, etc. It can also use comparator circuit, AND gate circuit and NAND gate circuit, consisting of other transistor, operational amplifier, comparator or digital circuit. Besides, it can use integrated circuit or discrete component circuit or various types of comparator circuits, AND gate circuit, NAND gate circuit and trigger circuit. Based on needs, various types of analog circuits, digital circuits or the combination of the two can be used, as well as circuits of any type which can complete this circuit function.

Figure 35:
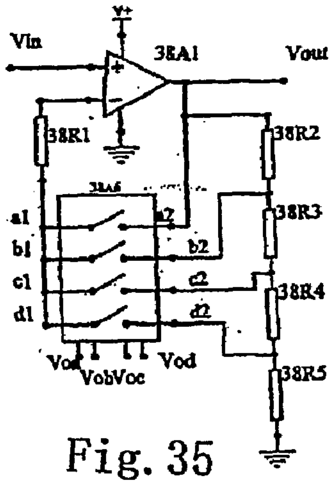
FIG. 35 is an amplifier circuit, whose amplification coefficient can be adjusted based on the receiving distance, used by an open-style active acoustic noise suppressing receiver according to the invention.

FIG. 35 shows an amplifier circuit, whose amplification coefficient can be adjusted based on the receiving distance, used by an open-style active acoustic noise suppressing receiver in the invention.

When the output terminals Voa, Vob, Voc and Vod of AND gate circuits 37*a*1, 137*a*12, 37*a*13 and 37*a*14 in FIG. 35 have high level output respectively, they will actuate the input ends Voa, Vob, Voc and Vod of the analog switches 38*a*6 to turn on a1 to a2, b1 to b2, c1 to c2 and d1 to d2 to allow the amplifier 38A1 having different amplification coefficients.

Figure 36:
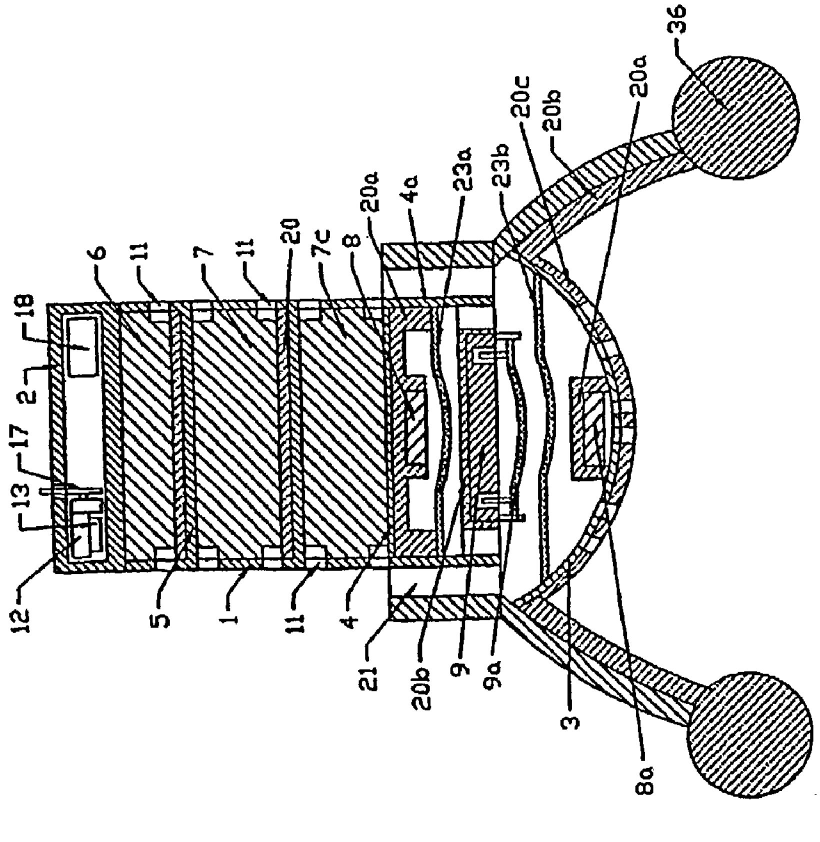
FIG. 36 is a sectional schematic view of an open-style active suppressing receiver according to the invention.

FIG. 36 is the sectional schematic view of an open-style active noise suppressing receiver of the invention.

Compared with FIGS. 15, 28 and 24, it differs from them in that: its noise-collecting module is the same as that in FIG. 28. The difference between its receiver module and that in FIGS. 15 and 24 lies in: in the receiver module in FIG. 24, feedback pickup 8*a* fixed with a sound-proof fixation anti-vibration pad 20*a* is placed between acoustically transparent diaphragm 23 and screen 3. Acoustic materials 20*b* and 20*c* are put on the surface under ear pad support 35 and screen 3 so that it becomes an against-the-ear noise suppressing receiver or ear muff noise suppressing receiver.

Figure 37:
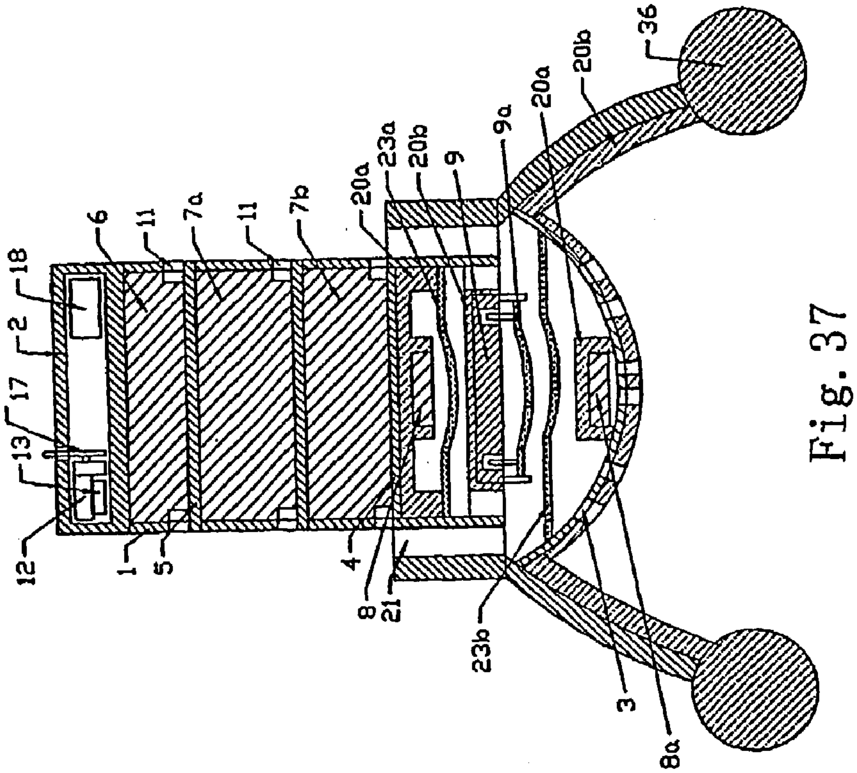
FIG. 37 is a sectional schematic view of an open-style active suppressing receiver according to the invention.

FIG. 37 is the sectional schematic view of an open-style active noise suppressing receiver of the invention.

Compared with FIGS. 29 and 36, it differs from them in that: its acoustic noise-canceling pickup 7 and 7*c* of the noise-collecting module are replaced by non-acoustic noise-canceling pickups 7*a* and 7*b* whose inlet hole is opened on the sidewall of cylinder and whose structure is approximately the same as that of environmental noise pickup 6. Other types of non-acoustic noise-canceling pickups can also be used.

Figure 38:
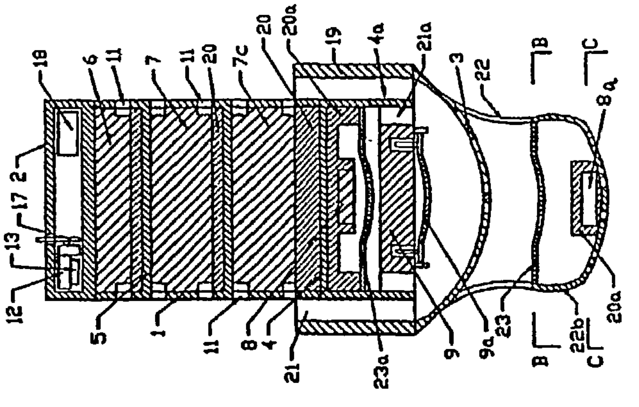
FIG. 38 is a sectional schematic view of an open-style active suppressing receiver according to the invention.
Figure 38B:
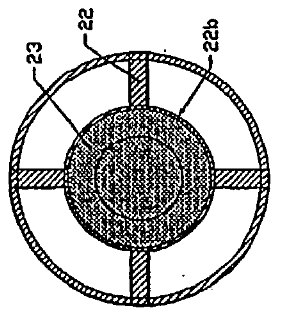
FIG. 38B is a sectional view along the line B—B shown in FIG. 38.

FIG. 38 is the sectional schematic view of an open-style active noise suppressing receiver of the invention embodiment and FIG. 38B is the sectional view along the line of B—B as shown in FIG. 38.

Compared with FIGS. 9, 28, 23, 24 and 36, it differs from them in that: its noise-collecting module is the same as that in FIG. 28. The difference between the receiver module and that in FIGS. 9, 24 and 36 lies in: the acoustically transparent diaphragm 23 in FIG. 9 is placed between the screen 3 and the diaphragm support 22*a* in the receiver module in FIG. 23 and feedback pickup 8*a* which can insulate sound and is fixed by sound-proof anti-vibration pad 20*a* is put between acoustically transparent diaphragm 23 and diaphragm support 22*a*. Feedback pickup 8*a* can receive sounds input from the sound hole on diaphragm support 22*a*. Screen 3 combines with the external wall of acoustic channel 21, rather than with the internal wall of cylinder 4*a*. Acoustic channel 21*a* is available between receiver 9 and the internal wall of cylinder 4*a*.

Figure 39:
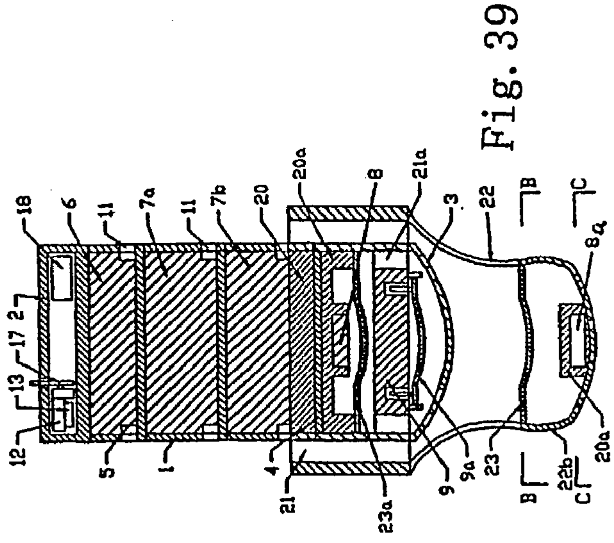
FIG. 39 is a sectional schematic view of an open-style active suppressing receiver according to the invention.
Figure 39B:
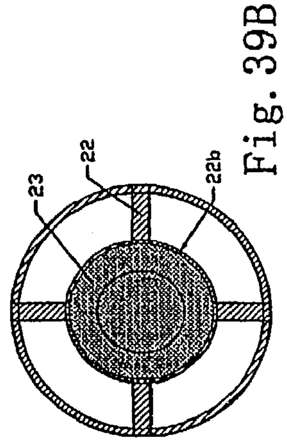
FIG. 39B is a sectional view along the line B—B shown in FIG. 39.

FIG. 39 is the sectional schematic view of an open-style active noise suppressing receiver of the invention embodiment and FIG. 39B is the sectional view along the line B—B as shown in FIG. 39.

Compared with FIGS. 37 and 38, it differs from them in that: its noise-collecting module is the same as that in FIG. 37. The difference between the receiver module and that in FIG. 38 lies in: screen 3 does not combine with the external wall of acoustic channel 21 but with the internal wall of cylinder 4*a*. Acoustic channel 21*a* is available between receiver 9 and the internal wall of cylinder 4*a*.

Due to the limited space, every new implementation combined by every component in the above every preferred embodiment of the invention can not be described one by one. Therefore, any kind of implementation formed by means of re-combining method should be included within the scope disclosed in the invention.

Every embodiment of the open-style active noise-suppressing receiver of the invention is only principal diagram. The actual shape of the shell, internal structure, the installation position of every component, parts to be used and the addition and the removal of those parts can be varied according to various objects of the receiver. For example, all the parameters can be designed according to the model and object of the receiver such as ear muffs receiver, ear wearing receiver, earphone, insert earphone, in-ear-phone, auditory meatus style or deep auditory meatus style phone and so on.

Although the invention has been explained by detailed descriptions of the preferred embodiments in connection with the accompany drawings as stated above, the invention is not limited to the disclosed embodiments. It will not difficult for those skilled in the art to make various improvements, modifications and substitutions to the noise-canceling pickup with a combined structure according to the invention, in the hints contained in the preferred embodiments within the spirits and the scope of the invention, which are only defined by the appended claims.

The invention claimed is:

1. A noise-suppressing receiver comprising:

a housing defined by a first end, a second end and a sidewall therebetween, said housing being divided into a noise suppressing chamber and a plurality of noise collecting chambers in a sequence from the first end to the second end, wherein each of said noise collecting chambers has a noise entrance formed on the sidewall of the housing;

a speaker placed in the noise suppressing chamber;

a first noise-canceling pickup placed in a noise collecting chamber adjacent to the noise suppressing chamber;

an environmental noise pickup placed in a noise collecting chamber close to the second end with its front surface facing the speaker.

2. A noise-suppressing receiver according to claim 1, wherein the housing has a cylindrical shape, the noise suppressing chamber and each of the plurality of noise collecting chambers are separated by a partition layer, respectively.

3. A noise-suppressing receiver according to claim 1, wherein the second end of the housing has a front cover, a printed circuit board including a working circuit and an infrared receiving-transmitting device is fixed on the internal surface of the front cover, and a volume adjuster is coupled to the working circuit.

4. A noise-suppressing receiver according to claim 3, characterized in that said working circuit includes an common-mode rejection circuit and/or an amplitude compensation circuit, and/or a phase shifter circuit, and/or a time delay circuit and/or a frequency compensation circuit.

5. A noise-suppressing receiver according to claim 3, characterized in that said working circuit further includes a window comparison circuit with multiple intervals, which can adjust the amplification coefficient of an amplifier in the noise-canceling pickup based on a receiving distance.

6. A noise-suppressing receiver according to claim 3, characterized in that the noise-canceling pickup in said noise-suppressing receiver includes an amplifier circuit, the amplification coefficient of the amplifier circuit is adjusted based on the receiving distance.

7. A noise-suppressing receiver according to claim 1, characterized in that it further includes an acoustically transparent diaphragm located in front of the speaker, a sound wave noise-suppressing chamber is formed between a vibrating diaphragm of the speaker and the acoustically transparent diaphragm.

8. A noise-suppressing receiver according to claim 1, characterized in that said noise-suppressing receiver is an earphone, an in-ear-phone, an auditory meatus style or a deep auditory meatus style small-size active noise-suppressing receiver.

9. A noise-suppressing receiver according to claim 1, further comprising a second noise-canceling pickup placed in a noise collecting chamber between the noise collecting chamber containing the first noise-canceling pickup and the noise collecting chamber containing the environmental noise pickup, wherein the front surfaces of the first and second noise-canceling pickups face the speaker.

10. A noise-suppressing receiver according to claim 9, wherein a screen covers the first end of the housing, and a feedback pickup is fixed on an internal surface of the screen.

11. A noise-suppressing receiver according to claim 1, further comprising a second noise-canceling pickup placed in the same noise collecting chamber that contains the environmental noise pickup, wherein the front surface of the first and second noise-canceling pickups faces the environmental noise pickup, and the second noise-canceling pickup is positioned between the first noise-canceling pickup and the environmental noise pickup.

12. A noise-suppressing receiver according to claim 1, wherein a screen covers the first end of the housing, a feedback pickup is fixed on an internal surface of the screen, and a noise entrance channel is formed on an outer surface of the sidewall the noise suppressing chamber.

13. A noise-suppressing receiver according to claim 1, wherein a part of the first noise-canceling pickup is placed in the noise collecting chamber adjacent to the noise suppressing chamber, another part, of the first noise-canceling pickup is placed in the noise collecting chamber that contains the environmental noise pickup, and a noise entrance channel is formed on an outer surface of the sidewall the noise suppressing chamber.

14. A noise-suppressing receiver comprising:

a housing defined by a first end, a second end, and a sidewall therebetween; said housing being divided into a noise suppressing chamber and a plurality of noise collecting chambers in a sequence from the first end to the second end, wherein each of said noise collecting chambers has a noise entrance formed on the sidewall of the housing;

a speaker placed in the noise suppressing chamber, an environmental noise pickup placed in a noise collecting chamber adjacent to the noise suppressing chamber with a front surface of the environmental noise pickup facing away from the speaker; and a first noise-canceling pickup placed in a noise collecting chamber close to the second end.

15. A noise-suppressing receiver according to claim 14, further comprising a second noise-canceling pickup placed in the noise collecting chamber containing the environmental noise pickup, wherein the front surface of the first noise-canceling pickup faces away from the speaker, the front surface of the second noise-canceling pickup faces the speaker.

* * * * *